(12) United States Patent
Yamahiro et al.

(10) Patent No.: US 7,129,370 B2
(45) Date of Patent: Oct. 31, 2006

(54) SILICON COMPOUND AND A PRODUCTION PROCESS FOR SILICON COMPOUND

(75) Inventors: Mikio Yamahiro, Kanagawa (JP); Hisao Oikawa, Kanagawa (JP); Kenya Ito, Kanagawa (JP); Masami Tanaka, Kanagawa (JP); Nobumasa Ootake, Kanagawa (JP); Kenichi Watanabe, Kanagawa (JP)

(73) Assignee: Chisso Corporation, Osaka (JP)

( * ) Notice: Subject to any disclaimer, the term of this patent is extended or adjusted under 35 U.S.C. 154(b) by 170 days.

(21) Appl. No.: 10/664,151

(22) Filed: Sep. 17, 2003

(65) Prior Publication Data

US 2005/0033077 A1    Feb. 10, 2005

(30) Foreign Application Priority Data

Sep. 17, 2002 (JP) .............................. 2002-270430
Feb. 28, 2003 (JP) .............................. 2003-053144

(51) Int. Cl.
C07F 7/04  (2006.01)
(52) U.S. Cl. ..................................................... 556/443
(58) Field of Classification Search ................. 556/443
See application file for complete search history.

(56) References Cited

OTHER PUBLICATIONS

"Orhani/Inorganic nanocomposite star poolymer via atom transfer Radical Polymerization of Methyl methacrylate Using octafunctional silsesquioxane cores", Macromolecules 2001, 34, p. 5398-5407.*
Fluoropolymerr Resists for 157 nm Lithography, Advance in Resist Technology and Processing XX, Jun. 2003.*

* cited by examiner

*Primary Examiner*—Samuel Barts
(74) *Attorney, Agent, or Firm*—Wenderoth, Lind & Ponack, L.L.P.

(57) ABSTRACT

The object of the present invention is to provide a new kind of silicon compound having an ester-type organic functional group and a new method for providing a $T_8$-silsesquioxane compound having a hydroxyl group by using said silicon compound as the starting material.

A silicon compound represented by formula (1) is obtained through the production process characterized by using a silicon compound represented by formula (2).

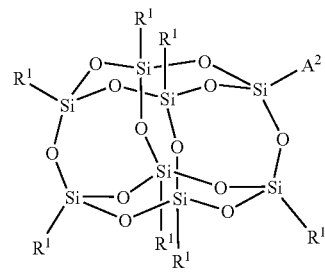

(1)

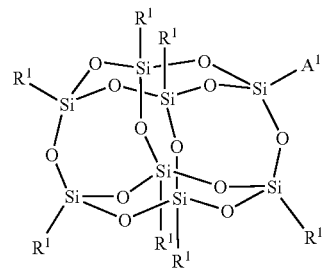

(2)

wherein:

in formula (1), each of seven $R^1$ group is independently selected from the group consisting of hydrogen, alkyl, substituted or unsubstituted aryl, and substituted or unsubstituted arylalkyl and $A^2$ is a hydroxyl-terminal organic functional group, and in formula (2), each of $R^1$ group is the same as $R^1$ in formula (1), and $A^1$ is an organic functional group containing an acyloxy group.

30 Claims, No Drawings

SILICON COMPOUND AND A PRODUCTION PROCESS FOR SILICON COMPOUND

FIELD OF THE INVENTION

The present invention relates to a novel synthetic process for a silicon compound having a hydroxyl group and having a well-defined structure. More specifically, it relates to a production process for a silsesquioxane compound having a hydroxyl group that is useful in applications including thermoplastic resin modifiers, layer insulators, encapsulants, coating materials and fire retardants by using a new type of silsesquioxane compound having an organic ester functional group as the starting material.

BACKGROUND OF THE INVENTION

A known method for introducing hydroxyl groups into a cage silsesquioxane compound composed of eight silicon atoms (referred to as "$T_8$-silsesquioxane compounds", hereinafter) comprises of the following steps: synthesis of the triflate-group containing silsesquioxane by the addition of trifluoromethanesulfonic acid to $T_8$-silsesquioxane containing eight intramolecular vinyl groups; and hydrolysis of said silsesquioxane in either acetone or dioxane in the presence of sodium carbonate (see, e.g., Patent Literature 1 and Nonpatent Literature 1).

However, approximately 85 to 90 percent of the resulting product prepared using the above-described method consists of trifluoromethansulfonic acid bound to only one vinyl group of each $T_8$-silsesquioxane molecule, leaving a proportion of $T_8$-silsesquioxane compounds unreacted. Therefore, the target compound must be isolated and purified from the mixture using techniques such as chromatography, resulting in a complicated process. In addition, the yield of the target compound tends to be low.

Patent Literature 1: U.S. Pat. No. 6,100,417.

Nonpatent Literature 1: Chemical Communications, 1289-(1999).

SUMMARY OF THE INVENTION

The object of the present invention is, therefore, to provide a brand-new silicon compound having an ester-type organic functional group and a novel production process for forming $T_8$-silsesquioxane compound having a hydroxyl group by using said silicon compound as the starting material.

The above-mentioned problems can be solved by the present invention with the composition as follows:

{1} A production process for a silicon compound represented by formula (1), characterized by using a silicon compound represented by formula (2),
wherein:

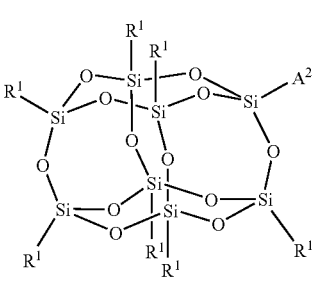

(1)

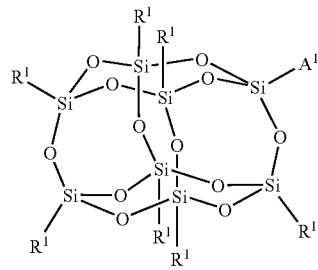

(2)

in formula (1), each of seven $R^1$ is a functional group independently selected from the group consisting of (a) hydrogen, (b) alkyl wherein each hydrogen may be optionally substituted with fluorine and each —$CH_2$— group may be optionally replaced with —O—, —CH=CH—, cycloalkylene or cycloalkenylene, (c) substituted or unsubstituted aryl, and (d) substituted or unsubstituted arylalkyl wherein each hydrogen of the alkylene group may be optionally substituted with fluorine and each —$CH_2$— group of said alkylene may be optionally replaced with —O— or —CH=CH—; and $A^2$ is a hydroxyl-terminal organic functional group, and in formula (2), each of $R^1$ is the same as $R^1$ in formula (1), and $A^1$ is an organic functional group containing an acyloxy group.

{2} The production process as described in the item {1}, wherein each of seven $R^1$ in formula (1) is independently selected from the group consisting of: hydrogen; $C_1$–$C_{45}$ alkyl wherein each hydrogen may be optionally substituted with fluorine and each —$CH_2$— group may be optionally replaced with —O—, —CH=CH—, cycloalkylene, or cycloalkenylene; substituted or unsubstituted aryl; and substituted or unsubstituted arylalkyl wherein each hydrogen of the alkylene is optionally substituted with fluorine and each —$CH_2$— group of said alkylene may be optionally replaced with —O— or —CH=CH—.

{3} The production process as described in the item {1}, wherein each of seven $R^1$ in formula (1) is independently selected from the group consisting of: hydrogen; and $C_1$–$C_{30}$ alkyl wherein each hydrogen may be optionally substituted with fluorine, and each —$CH_2$— group may be optionally replaced with —O— or cycloalkylene.

{4} The production process as described in the item {1}, wherein each of seven $R^1$ in formula (1) is independently selected from the group consisting of: $C_1$–$C_{20}$ alkenyl wherein each hydrogen may be optionally substituted with fluorine and each —$CH_2$— group may be optionally replaced with —O— or cycloalkylene; and $C_1$–$C_{20}$ alkyl wherein each —$CH_2$— group is optionally replaced with cycloalkenylene and in the —$CH_2$— group optionally replaced with cycloalkylene, each hydrogen may be optionally substituted with fluorine.

{5} The production process as described in the item {1}, wherein each of seven $R^1$ in formula (1) is independently selected from the group consisting of: naphthyl; and phenyl wherein each hydrogen may be optionally substituted with halogen or $C_1$–$C_{10}$ alkyl where each hydrogen may-be optionally substituted with fluorine and each —$CH_2$— group may be optionally replaced with —O—, —CH=CH—, cycloalkylene or phenylene.

{6} The production process as described in the item {1}, wherein each of seven $R^1$ in formula (1) is independently selected from the group consisting of phenylalkyls: wherein each hydrogen atom in a benzene ring may be optionally substituted with halogen or $C_1$–$C_{12}$ alkyl where each hydrogen may be optionally substituted with fluorine and each —$CH_2$— group may be optionally replaced with —O—, —CH=CH—, cycloalkylene or phenylene, and in the alkylene of the phenylalkyl, the number of carbons of the alkylene group is 1 to 12; each hydrogen of said alkylene group may be optionally substituted with fluorine; and each —$CH_2$— group of said alkylene group may be optionally replaced with —O— or —CH=CH—.

{7} The production process as described in the item {1}, wherein each of seven $R^1$ in formula (1) is independently selected from the group consisting of; $C_1$–$C_8$ alkyl wherein each hydrogen may be optionally substituted with fluorine and each —$CH_2$— group may be optionally replaced with —O—, —CH=CH—, cycloalkylene or cycloalkenylene; phenyl wherein each hydrogen may be optionally substituted with halogen, methyl or methoxy; unsubstituted naphthyl; and phenylalkyl wherein (a) each phenyl hydrogen may be optionally substituted with fluorine, $C_1$–$C_4$ alkyl, ethenyl or methoxy, (b) the number of carbons of the alkylene is 1 to 8, and each —$CH_2$— group of said alkylene may be optionally replaced with —O— or —CH=CH—.

{8} The production process as described in the item {1}, wherein all of seven $R^1$ in formula (1) are the same functional groups selected from the group consisting of: $C_1$–$C_8$ alkyl wherein each hydrogen may be optionally substituted with fluorine and each —$CH_2$— group may be optionally replaced with —O—, —CH=CH—, cycloalkylene or cycloalkenylene; phenyl wherein each hydrogen may be optionally substituted with halogen, methyl or methoxy; unsubstituted naphthyl; and phenylalkyl wherein (a) each phenyl hydrogen may be optionally substituted with fluorine, $C_1$–$C_4$ alkyl, ethenyl or methoxy, (b) the number of carbons of the alkylene is 1 to 8, and each —$CH_2$— group of said alkylene may be optionally replaced with —O— or —CH=CH—.

{9} The production process as described in the item {1}, wherein all of seven $R^1$ in formula (1) are the same functional groups selected from $C_1$–$C_8$ alkyls wherein each hydrogen may be optionally substituted with fluorine and each —$CH_2$— group may be optionally replaced with —O—, —CH=CH—, cycloalkylene, or cycloalkenylene.

{10} The production process as described in the item {1}, wherein all of seven $R^1$ in formula (1) are the same functional groups selected from the group consisting of: phenyl wherein each hydrogen may be optionally substituted with halogen, methyl or methoxy; naphthyl; and phenylalkyl wherein (a) each hydrogen of the phenyl may be substituted with fluorine, $C_1$–$C_4$ alkyl, ethenyl or methoxy, (b) the number of carbons of the alkylene group is 1 to 8, and each —$CH_2$— group of said alkylene may be optionally replaced with —O—.

{11} The production process as described in the item {1}, wherein $A^2$ in formula (1) is a group represented by formula (3), and $A^1$ in formula (2) is a group represented by formula (4),

  (3)

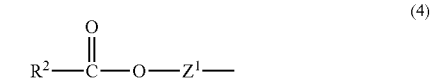  (4)

wherein:

in formula (3), $Z^1$ is (a) $C_1$–$C_{22}$ alkylene where each —$CH_2$— may be optionally replaced with —O—, or (b) $C_3$–$C_8$ alkenylene where each —$CH_2$— may be optionally replaced with —O—; and in formula (4), $R^2$ is selected from the group of $C_1$–$C_{17}$ alkyl where each hydrogen may be optionally substituted with fluorine, $C_2$–$C_3$ alkenyl, substituted or unsubstituted phenyl and unsubstituted phenylalkyl.

{12} The production process as described in the item {1}, wherein $A^2$ in formula (1) is a group represented by formula (5), and $A^1$ in formula (2) is a group represented by formula (6),

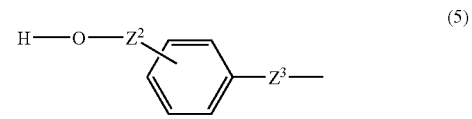  (5)

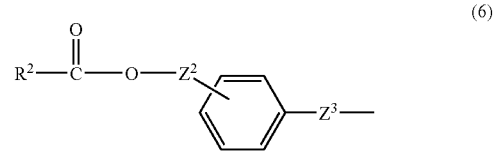  (6)

wherein:

in formula (5), (a) $Z^2$ represents a single bond or $C_1$–$C_3$ alkylene and may be bound to the benzene ring at any position, (b) $Z^3$ is (i) $C_1$–$C_{22}$ alkylene where each —$CH_2$— may be optionally replaced with —O— or (ii) $C_3$–$C_8$ alkenylene where each —$CH_2$— may be optionally replaced with —O—, and in formula (6), $R^2$ is selected from the group consisting of $C_1$–$C_{17}$ alkyl, $C_2$–$C_3$ alkenyl, substituted or unsubstituted phenyl and unsubstituted phenylalkyl, and $Z^2$ and $Z^3$ are the same as $Z^2$ and $Z^3$ in formula (5).

{13} The production process as described in the item {11}, wherein: $Z^1$ in formula (3) is $C_1$–$C_{22}$ alkylene where each —$CH_2$— group may be optionally replaced with —O—; and $R^2$ in formula (4) is selected from the group consisting of $C_1$–$C_{17}$ alkyl where each hydrogen may be optionally substituted with fluorine, and $C_2$–$C_3$ alkenyl where each —$CH_2$— group may be optionally replaced with —O—.

{14} The production process as described in the item {11}, wherein $Z^1$ in formula (3) is $C_1$–$C_6$ straight-chain alkylene where each —$CH_2$— group may be optionally replaced with —O—; and $R^2$ in formula (4) is methyl.

{15} The production process as described in the item {12}, wherein $Z^2$ in formula (5) represents a single bond or $C_1$–$C_3$ alkylene where each —$CH_2$— group may be optionally replaced with —O—, and $Z^3$ is $C_1$–$C_{22}$ alkylene where each —$CH_2$— group may be optionally replaced with —O— and may be bound to the benzene ring at any carbon position; and $R^2$ in formula (6) is selected from the group consisting of (a) $C_1$–$C_{17}$ alkyl where each hydrogen may be optionally substituted with fluorine and each —$CH_2$— group may be optionally replaced with —O—, and (b) $C_2$–$C_3$ alkenyl where each —$CH_2$— group may be optionally replaced by —O—.

{16} The production process as described in the item {12}, wherein $Z^2$ in formula (5) represents a single bond or —$CH_2$—, $Z^3$ in formula (5) is —$C_2H_4$—, and $R^2$ in formula (6) is methyl.

{17} The production process as described in the item {1}, wherein all of seven $R^1$ in formula (1) are the same groups selected from the group consisting of ethyl, 2-methylpropyl, 2,4,4-trimethylpentyl, cyclopentyl, cyclohexyl, trifluoropropyl, tridecafluoro-1,1,2,2-tetrahydrooctyl, and unsubstituted phenyl.

{18} The production process as described in the item {1}, wherein all of seven $R^1$ in formula (1) are either unsubstituted phenyl or trifluoropropyl.

{19} A silicon compound represented by formula (2),

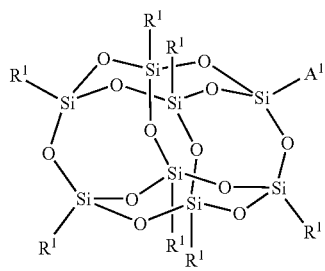

(2)

wherein: in formula (2), each of seven $R^1$ is independently selected from the group consisting of (a) hydrogen, (b) alkyl where each hydrogen may be optionally substituted with fluorine and each —$CH_2$— group may be optionally replaced with —O—, —CH=CH—, cycloalkylene or cycloalkenylene, (c) substituted or unsubstituted aryl, and (d) substituted or unsubstituted arylalkyl where each hydrogen of the alkylene may be optionally substituted with fluorine and each —$CH^2$— group of said alkylene may be optionally replaced with —O— or —CH=CH—; and $A^1$ is an organic group that has an acyloxy group.

{20} The silicon compound as described in the item {19}, wherein $A^1$ in formula (2) is a group represented by formula (4),

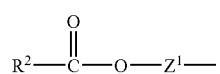

(4)

wherein: in formula (4), $R^2$ is selected from the group consisting of (a) $C_1$–$C_{17}$ alkyl where each hydrogen may be optionally substituted with fluorine, (b) $C_2$–$C_3$ alkenyl, (c) substituted or unsubstituted phenyl and (d) unsubstituted phenylalkyl; and $Z^1$ is either $C_1$–$C_{22}$ alkylene where each —$CH_2$— group may be optionally replaced with —O—, or $C_3$–$C_8$ alkenylene where each —$CH_2$— group may be optionally replaced by —O—.

{21} The silicon compound as described in the item {19}, wherein $A^1$ in formula (2) is a group represented by formula (6),

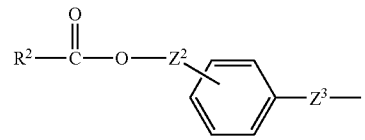

(6)

wherein: in formula (6), $R^2$ is selected from the group consisting of $C_1$–$C_{17}$ alkyl; $C_2$–$C_3$ alkenyl; substituted or unsubstituted phenyl and unsubstituted phenylalkyl; and $Z^2$ represents a single bond or $C_1$–$C_3$ alkylene that may be bound to the benzene ring at any carbon position; and $Z^3$ is either $C_1$–$C_{22}$ alkylene where each —$CH_2$— group may be optionally replaced with —O—, or $C_3$–$C_8$ alkenylene where each —$CH_2$— may be optionally replaced by —O—.

{22} The production process as described in the item {1}, characterized by providing a silicon compound represented by formula (2) through reacting a trichlorosilane compound having an acyloxy group with either (a) a compound represented by formula (7) or (b) a compound represented by formula (12) and acid-catalyzed transesterificating in alcohol,

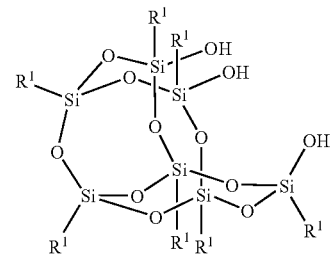

(7)

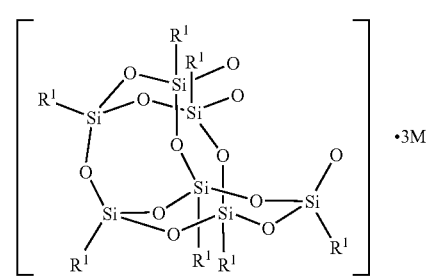

(12)

wherein: in formulas (7) and (12), $R^1$ is the same as $R^1$ in formula (1) and M is a monovalent alkali metal atom.

{23} The production process as described in the item {11}, characterized by providing a silicon compound represented by formula (10) through reacting a compound represented by formula (8) with a compound represented by formula (7) and acid-catalyzed transesterificating in alcohol, (7)
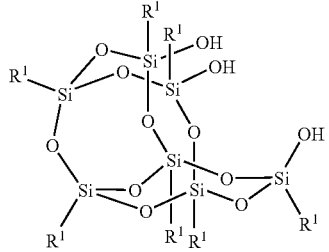

(8)
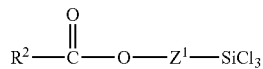

(10)
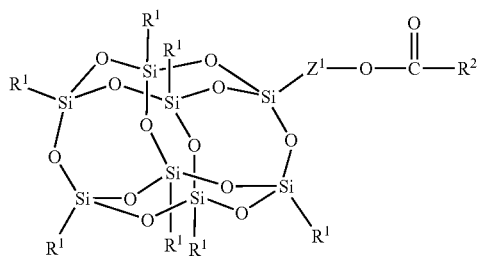

wherein: in formula (7), $R^1$ is the same as $R^1$ in formula (1) as described in the item {1}, in formula (8), $R^2$ and $Z^1$ are the same as $R^2$ and $Z^1$ in formula (4) as described in the item {11}, and in formula (10), $R^1$, $R^2$ and $Z^1$ are the same as $R^1$, $R^2$ and $Z^1$ in formulas (7) and (8).

{24} The production process as described in the item {12}, characterized by providing a silicon compound represented by formula (11) through reacting a compound represented by formula (9) with a compound represented by formula (7) and acid-catalyzed transesterificating in alcohol, (7)
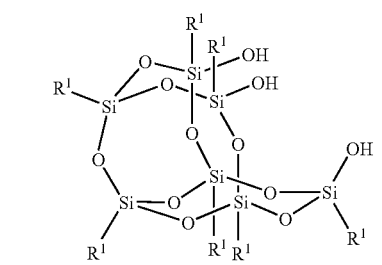

(9)
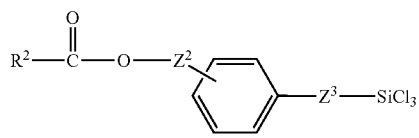

-continued

(11)
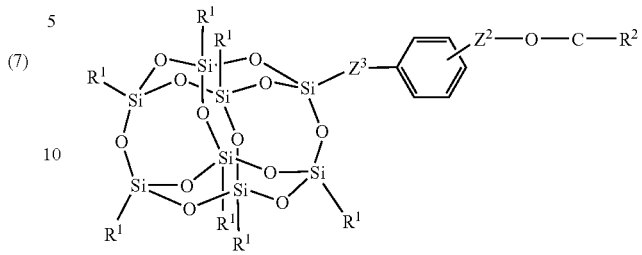

wherein: in formula (7), $R^1$ is the same as $R^1$ in formula (1) as described in the item {1}, in formula (9), $R^2$, $Z^2$, and the binding position thereof to the benzene ring are the same as $R^2$, $Z^2$, and the binding position thereof to the benzene ring in formula (6) as described in the item {12}, and in formula (11), the characters and the binding position thereof to the benzene ring are the same as the characters and the binding position thereof to the benzene ring in formulas (7) and (9).

{25} The production process as described in the item {11}, characterized by providing a silicon compound represented by formula (10) through reacting a compound represented by formula (8) with a compound represented by formula (7) and acid-catalyzed transesterificating in alcohol, (7)
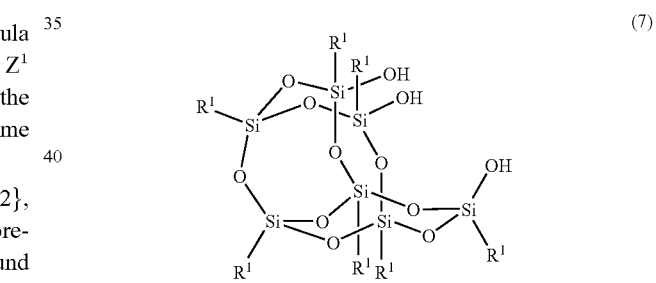

(8)
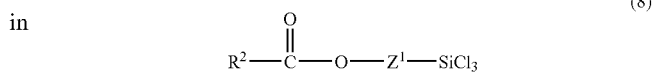

(10)
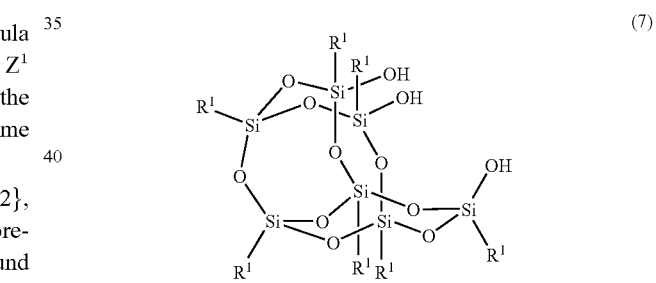

wherein: in formula (7), all of seven $R^1$ are the same functional groups selected from the group consisting of ethyl, 2-methylpropyl, 2,4,4-trimethylpentyl, cyclopentyl, cyclohexyl, trifluoropropyl, tridecafluoro-1,1,2,2-tetrahydrooctyl and unsubstituted phenyl, in formula (8), $R^2$ and $Z^1$ are the same as $R^2$ and $Z^1$ in formula (4) as described in the item {11}, and in formula (10), $R^1$, $R^2$ and $Z^1$ are the same as $R^1$, $R^2$ and $Z^1$ in formula (7) and (8).

{26} The production process as described in the item {11}, characterized by providing a silicon compound represented by formula (10) through reacting a compound represented by formula (8) with a compound represented by formula (12) and acid-catalyzed transesterificating in alcohol,

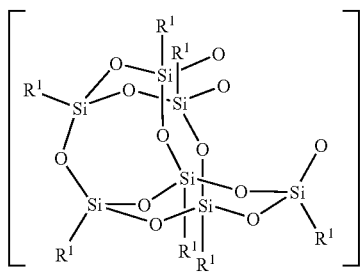
(12)

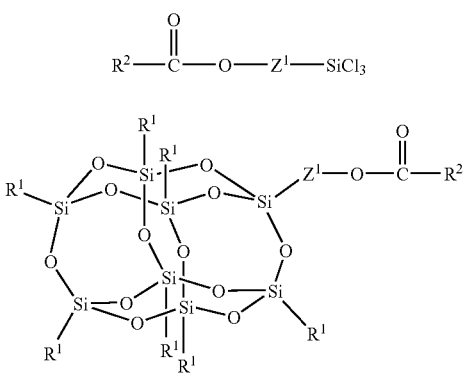
(8)
(10)

wherein: in formula (12), $R^1$ is the same as $R^1$ in formula (1) as described in the item {1} and M is a monovalent alkali metal atom, in formula (8), $R^2$ and $Z^1$ are the same as $R^2$ and $Z^1$ in formula (4) as described in the item {11}, and in formula (10), $R^1$, $R^2$, and $Z^1$ are the same as $R^1$, $R^2$, and $Z^1$ in formulas (12) and (8).

{27} The production process as described in the item {12}, characterized by providing a silicon compound represented by formula (11) through reacting a compound represented by formula (9) with a compound represented by formula (12) and acid-catalyzed transesterificating in alcohol,

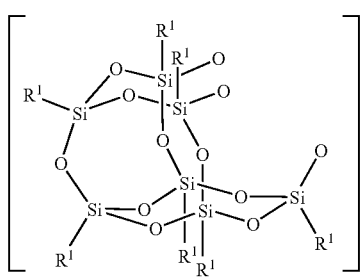
(12)

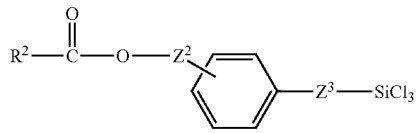
(9)

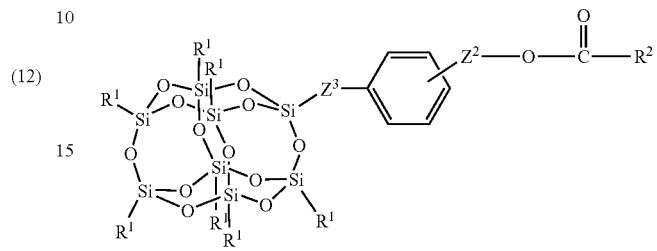
(11)

wherein: in formula (12), $R^1$ is the same as $R^1$ in formula (1) as described in the item {1} and M is a monovalent alkali metal atom, in formula (9), $R^2$, $Z^2$, $Z^3$, and the binding position thereof to the benzene ring are the same as $R^2$, $Z^2$, $Z^3$, and the binding position thereof to the benzene ring in formula (6) as described in the item {12}, and in formula (11), the characters and the binding position thereof to the benzene ring are the same as the characters and the binding position thereof to the benzene ring in formulas (12) and (9).

{28} The production process as described in the item {11}, characterized by providing a silicon compound represented by formula (10) through reacting a compound represented by formula (8) with a compound represented by formula (12) and acid-catalyzed transesterificating in alcohol,

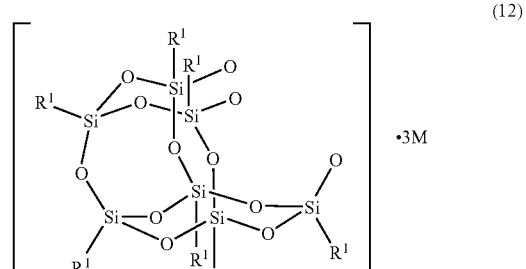
(12)

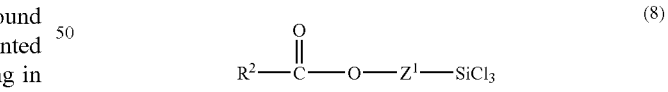
(8)

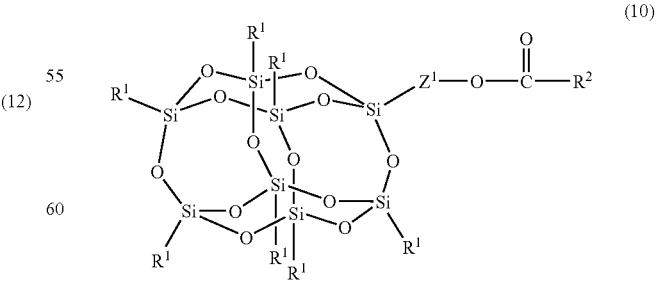
(10)

wherein: in formula (12), all of seven $R^1$ are the same groups selected from the group consisting of (i) $C_1$–$C_8$ alkyl where each hydrogen may be optionally substituted with fluorine and each —CH$_2$— group may be optionally replaced with —O—, —CH=CH—, cycloalkylene or cycloalkenylene, (ii) phenyl where each hydrogen may be optionally substituted with halogen, methyl or methoxy, (iii) unsubstituted naphthyl and (iv) phenylalkyl where (A) each benzene hydrogen may be substituted with fluorine, C$_1$–C$_4$ alkyl, ethenyl or methoxy, (B) each —CH$_2$— group of the alkylene may be optionally replaced with —O— or —CH=CH—, and M is a monovalent alkali metal atom, in formula (8), R$^2$ and Z$^1$ are the same as R$^2$ and Z$^1$ in formula (4) as described in the item {11}, and in formulas (12) and (8).

{29} The production process as described in the item {11}, characterized by providing a silicon compound represented by formula (10) through reacting a compound represented by formula (8) with a compound represented by formula (12) and acid-catalyzed transesterificating in alcohol,

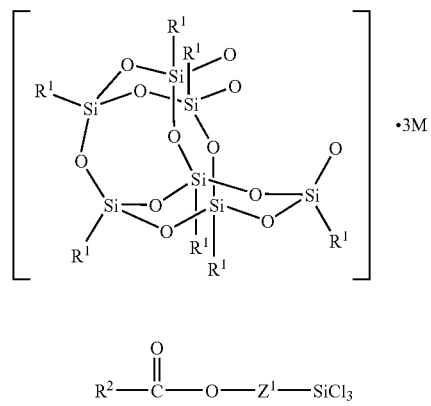

(12)

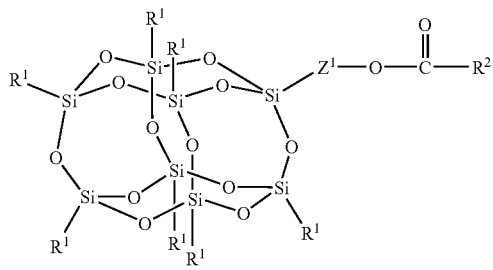

(8)

(10)

wherein: in formula (12), all of seven R$^1$ are the same groups selected from the group consisting of (i) ethyl, (ii) 2-methylpropyl, (iii) 2,4,4,-trimethylpentyl, (iv) cyclopentyl, (v) cyclohexyl, (vi) trifluoropropyl, (vii) tridecafluoro-1,1,2,2-tetrahydrooctyl, and (viii) unsubstituted phenyl, and M is a monovalent alkali metal atom, in formula (8), R$^2$ and Z$^1$ are the same as R$^2$ and Z$^1$ in formula (4) as described in the item {11} of formula (10), R$^1$, defined below through reaction of (a) a compound of formula (12), and in formula (10), R$^1$, R$^2$ and Z$^1$ are the same as R$^1$, R$^2$ and Z$^1$ in formulas (12) and (8).

{30} The production process as described in the item {12}, characterized by providing a silicon compound represented by formula (11) through reacting a compound represented by formula (9) with a compound represented by formula (12) and acid-catalyzed transesterificating in alcohol,

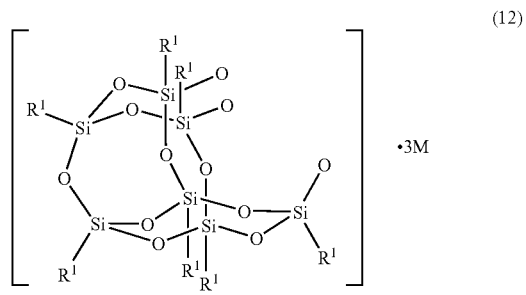

(12)

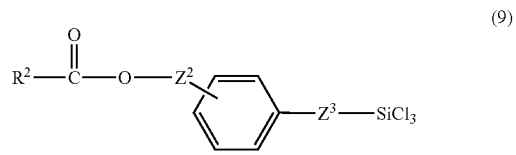

(9)

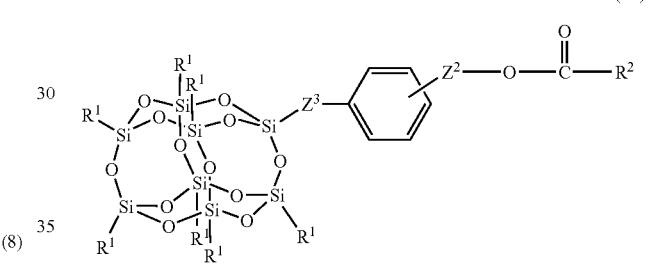

(11)

wherein: in formula (12), all of seven R$^1$ are the same groups selected from the group consisting of (i) C$_1$–C$_8$ alkyl wherein each hydrogen may be optionally substituted with fluorine and each —CH$_2$— group may be optionally replaced with —O—, —CH=CH—, cycloalkylene or cycloalkenylene, (ii) phenyl wherein each hydrogen may be optionally substituted with halogen, methyl or methoxy, (iii) unsubstituted naphthyl and (iv) phenylalkyl wherein each benzene hydrogen is optionally substituted with fluorine, C$_1$–C$_4$ alkyl, ethenyl or methoxy and each —CH$_2$— group of the akylene may be optionally replaced with —O— or —CH=CH—, and M is a monovalent alkali metal atom, in formula (9), R$^2$, Z$^2$, Z$^3$, and the binding position thereof to the benzene ring and are the same as R$^2$, Z$^2$, Z$^3$, and the binding position thereof to the benzene ring in formula (6) as described in the item {12}, and in formula (11), the characters and the binding position thereof to the benzene ring are the same as the characters and the binding position thereof to the benzene ring in formulas (12) and (9).

{31} The production process as described in the item {12}, characterized by providing a silicon compound represented by formula (11) through reacting a compound represented by formula (9) with a compound represented by formula (12) and acid-catalyzed transesterificating in alcohol,

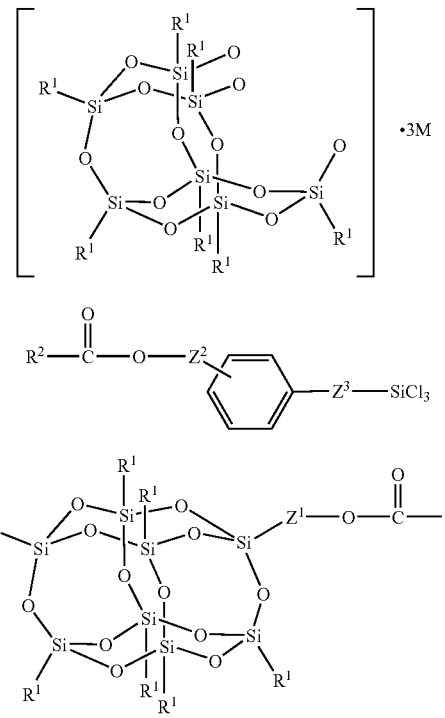

wherein: in formula (12), all of seven R¹ are the same groups selected from the group consisting of (i) ethyl, (ii) 2-methylpropyl, (iii) 2,4,4-trimethylpentyl, (iv) cyclopentyl, (v) cyclohexyl, (vi) trifluoropropyl, (vii) tridecafluoro-1,1,2,2-tetrahydrooctyl and (viii) unsubstituted phenyl, and M is a monovalent alkali metal atom, in formula (9), R², Z², Z³, and the binding position thereof to the benzene ring are the same as R², Z², Z³, and the binding position thereof to the benzene ring in formula (6) as described in the item {12}, and in formula (11), the characters and the binding position thereof to the benzene ring are the same as the characters and the binding position thereof to the benzene ring in formulas (12) and (9).

{32} The production process as described in the item {12}, characterized by providing a silicon compound represented by formula (11) through reacting a compound represented by formula (9) with a compound represented by formula (12) and acid-catalyzed transesterificating in alcohol,

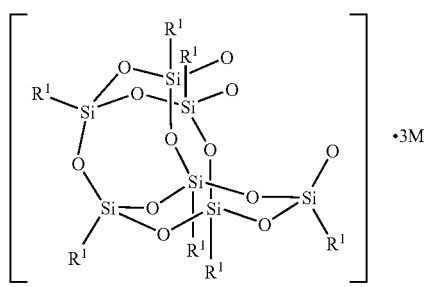

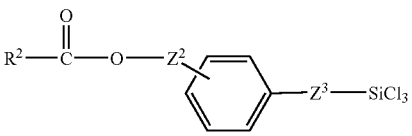

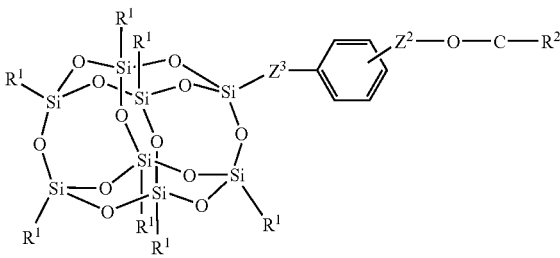

wherein: in formula (12), all of seven R¹ are either unsubstituted phenyl or trifluoropropyl and M is a monovalent alkali metal atom, in formula (9), R², Z², Z³, and the binding position thereof to the benzene ring are the same as R², Z², Z³, and the binding position thereof to the benzene ring in formula (6) as described in the item {12}, and in formula (11), the characters and the binding position thereof to the benzene ring are the same as the characters and the binding position thereof to the benzene ring in formulas (12) and (9).

{33} A silicon compound represented by formula (1), being prepared from a silicon compound represented by formula (2),

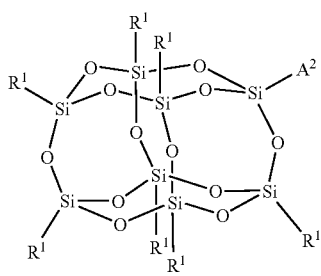

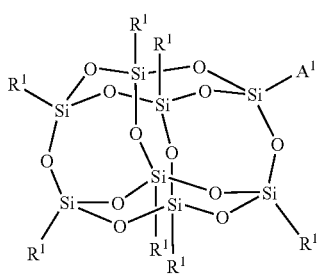

wherein: in formula (1), each of seven R¹ is independently selected from the group consisting of (a) hydrogen, (b) $C_1$–$C_{45}$ alkyl wherein each hydrogen may be optionally substituted with fluorine and each —$CH_2$— group may be optionally replaced with —O—, —CH=CH—, cycloalkylene or cycloalkenylene, (c) substituted or unsubstituted aryl and (d) substituted or unsubstituted arylalkyl wherein each hydrogen of the alkenylene may be optionally substituted with fluorine and each —CH$_2$— group of said alkenylene may be optionally replaced with —O— or —CH=CH—; and A$^2$ is a hydroxyl-terminal organic group, and in formula (2), R$^1$ is the same as R$^1$ in formula (1) and A$^1$ is an organic compound having an acyloxy group.

{34} The silicon compound as described in the item {33}, (a) in formula (1), all of seven R$^1$ are the same functional groups selected from the group consisting of (i) ethyl, (ii) 2-methylpropyl, (iii) 2,4,4-trimethylpentyl, (iv) cyclopentyl, (v) cyclohexyl, (vi) trifluoropropyl, (vii) tridecafluoro-1,1,2,2,-tetrahydrooctyl and (viii) unsubstituted phenyl; (b) A$^2$ is a group represented by formula (3) and (c) A$^1$ in formula (2) is a group represented by formula (4),

  (3)

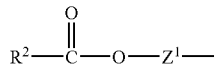  (4)

wherein: in formula (3), Z$^1$ is either C$_1$–C$_{22}$ alkylene where each —CH$_2$— group may be optionally replaced with —O—, or C$_3$–C$_8$ alkenylene where each —CH$_2$— group may be optionally replaced with —O—; in formula (4), R$^2$ is selected from the group consisting of C$_1$–C$_{17}$ alkyl where each hydrogen may be optionally substituted with fluorine, C$_2$–C$_3$ alkenyl, substituted or unsubstituted phenyl and unsubstituted phenylalkyl, and Z$^1$ is the same as Z$^1$ in formula (3).

{35} The silicon compound as described in the item {33}, (a) in formula (1), all of seven R$^1$ are the same functional groups selected from the group consisting of (i) ethyl, (ii) 2-methylpropyl, (iii) 2,4,4-trimethylpentyl, (iv) cyclopentyl, (v) cyclohexyl, (vi) trifluoropropyl, (vii) tridecafluoro-1,1,2,2,-tetrahydrooctyl and (viii) unsubstituted phenyl; (b) A$^2$ is a group represented by formula (5) and (c) A$^1$ in formula (2) is a group represented by formula (6),

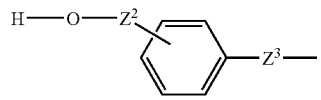  (5)

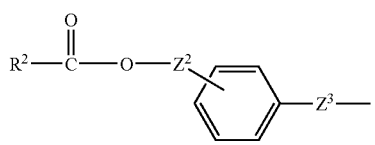  (6)

wherein: in formula (5), (A) Z$^2$ represents a single bond or C$_1$–C$_3$ alkylene and may be bound to the benzene ring at any carbon position, (B) Z$^3$ is either C$_1$–C$_{22}$ alkylene where each —CH$_2$— may be optionally replaced with —O—, or C$_3$–C$_8$ alkenylene where each —CH$_2$— may be optionally replaced with —O—, in formula (6), R$^2$ is selected from the group consisting of C$_1$–C$_{17}$ alkyl, C$_2$–C$_3$ alkenyl, substituted or unsubstituted phenyl and unsubstituted phenylalkyl, and Z$^2$ and Z$^3$ are the same as Z$^2$ and Z$^3$ in formula (5).

{36} The silicon compound as described in the item {34}, wherein all of seven R$^1$ are either unsubstituted phenyl or trifluoropropyl.

{37} The silicon compound as described in the item {35}, wherein all of seven R$^1$ are either unsubstituted phenyl or trifluoropropyl.

{38} The production process as described in the item {12}, characterized by providing a silicon compound represented by formula (11) through reacting a compound represented by formula (9) with a compound represented by formula (7) and acid-catalyzed transesterificating in alcohol,

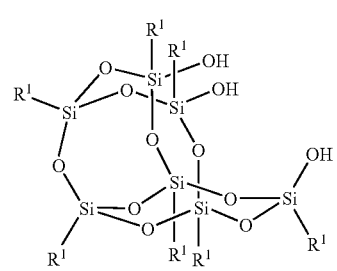  (7)

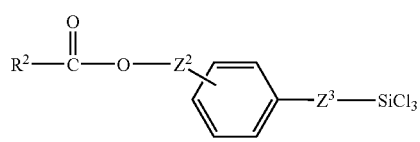  (9)

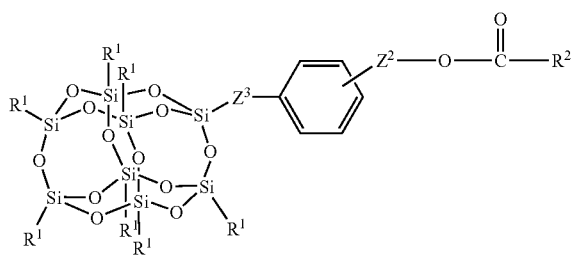  (11)

wherein: in formula (7), all of seven R$^1$ are the same group selected from the group consisting of (i) ethyl, (ii) 2-methylpropyl, (iii) 2,4,4-trimethylpentyl, (iv) cyclopentyl, (v) cyclohexyl, (vi) trifluoropropyl, (vii) tridecafluoro-1,1,2,2-tetrahydrooctyl and (viii) unsubstituted phenyl, in formula (9), R$^2$, Z$^2$, Z$^3$, and the binding position thereof to the benzene ring are the same as R$^2$, Z$^2$, Z$^3$, and the binding position thereof to the benzene ring in formula (6) as described in the item {12}, and in formula (11), the characters and the binding position thereof to the benzene ring are the same as the characters and the binding position thereof to the benzene ring in formulas (7) and (9).

EFFECTS: The method according to the invention allows the simplified production of silsequioxane compounds with hydroxyl groups. Silsesquioxane compounds of this type are extremely useful as a precursor to derive many types of silsesquioxane compounds. Hydroxyl groups of those silsesquioxane compounds can increase solubilities of T$_8$-silsesquioxane compounds in organic solvents, and mutual solubilities of resins in the preparation of organic-inorganic composite materials. Therefore, T$_8$-silsesquioxane compounds having hydroxyl groups according to the invention are useful not only as precursors to derive many types of silsesquioxanes, but also as resin modifiers.

DETAILED DESCRIPTION OF THE INVENTION

The terms used in the invention are defined as follows: both "alkyl" and "alkylene" may be straight-chained and branched groups. This applies to the cases where each hydrogen of said groups is optionally replaced with halogens or cyclic compounds and where each —CH$_2$— group of said groups is optionally replaced with —O—, —CH═CH—, cycloalkylene, cycloalkenylene or phenylene. If two or more hydrogen atoms or —CH$_2$— groups have been substituted, the substituents can be the same or different from each other. In an alkyl group, for example, two —CH$_2$— groups have been replaced with —O— and —CH═CH—, the said group represents either alcoxyalkenyl or alkenyloxyalkyl. In this case, the groups of alcoxy, alkenylene, alkenyl and alkylene can be straight-chained or branched. However, there must not be consequent —CH$_2$— groups between substituents of —O— in alkyl or alkylene groups.

Hereinafter, there are cases in which a compound in formula (1) is represented as a compound (1). The same applies to other compounds in other formulas. The production process for a compound (1) according to the present invention is characterized by using a compound (2).

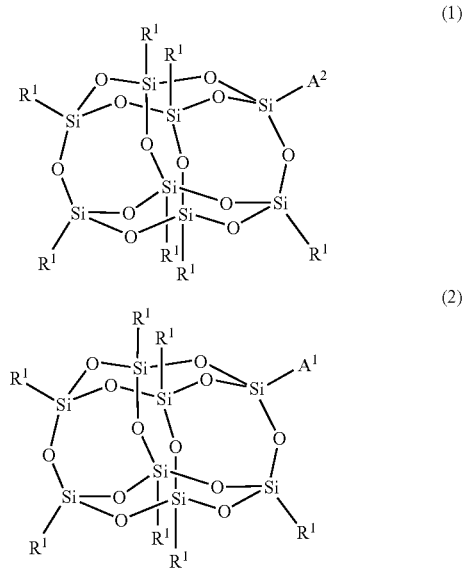

That is, R$^1$ in formula (2) is the same as R$^1$ in formula (1). In formula (1), each of seven R$^1$ is independently selected from the group consisting of hydrogen, alkyl groups, substituted or unsubstituted aryl groups, and substituted or unsubstituted arylalkyl groups. All of seven R$^1$ groups are preferably the same, but may be of two or more different groups. The latter case includes: two or more alkyl groups; two or more aryl groups; two or more aralkyl groups; a combination of hydrogen and at least one aryl group; a combination of at least one alkyl group and at least one aryl group; a combination of at least one alkyl group and at least one aralkyl group; and a combination of at least one aryl group and at least one aralkyl group. A compound of formula (1) where R$^1$ comprises of two or more different groups is prepared from two or more different raw materials, which are described thereinafter.

When R$^1$ is alkyl, the number of carbons is between 1 and 45. It should be preferably between 1 and 30, and more preferably between 1 and 8. In the alkyl groups, each hydrogen may be optionally substituted with fluorine and each —CH$_2$— group may be optionally replaced with —O—, —CH═CH—, cycloalkylene or cycloalkenylene. Preferred examples of alkyl groups include unsubstituted C$_1$–C$_{30}$ alkyl, C$_2$–C$_{29}$ alcoxyalkyl, C$_1$–C$_8$ alkyl where one —CH$_2$— group is replaced with cycloalkylene, C$_2$–C$_{20}$ alkenyl, C$_2$–C$_{20}$ alkenyloxyalkyl, C$_2$–C$_{20}$ alkyloxyalkenyl, C$_1$–C$_8$ alkyl where one —CH$_2$— group is replaced with cycloalkylene, and fluorinated compounds thereof. The number of carbons for said cycloalkylene and cycloalkenylene should be preferably between 3 and 8.

Examples of unsubstituted C$_1$–C$_{30}$ alkyl include methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl, and triacontyl. Examples of fluorinated C$_1$–C$_{30}$ alkyl include 3,3,3-trifluoropropyl, 3,3,4,4,5,5,6,6,6-nonadecafluorohexyl, tridecafluoro-1,1,2,2-tetrahydrooctyl, heptadecafluoro-1,1,2,2,-tetrahydrodecyl, perfluoro-1H,1H,2H,2H-dodecyl, and perfluoro-1H,1H,2H,2H-tetradecyl. Examples of C$_2$–C$_{29}$ alcoxyalkyl include 3-methyxypropyl, methoxyethoxyundecyl, and 3-heptafluoroisopropoxypropyl. Examples of C$_1$–C$_8$ alkyl where one —CH$_2$— group is replaced with cycloalkylene include cyclohexylmethyl, adamantaneetyl, cyclopentyl, cyclohexyl, 2-bicycloheptyl, and cyclooctyl. Cyclohexyl is an example where one —CH$_2$— group of methyl is replaced with cyclohexylene. Cyclohexylmethyl is an example where one —CH$_2$— group of ethyl is replaced with cyclohexylene.

Examples of C$_2$–C$_{20}$ alkenyl include ethenyl, 2-propenyl, 3-butenyl, 5-hexenyl, 7-octenyl, 10-undecenyl, and 21-dococenyl. Examples of C$_2$–C$_{20}$ alkenyloxyalkyl include aryloxyundecyl. Examples of C$_1$–C$_8$ alkyl where one —CH$_2$— group is replaced with cycloalkenylene include 2-(3-cyclohexenyl)ethyl, 5-(bicycloheptenyl)ethyl, 2-cyclopentenyl, 3-cyclohexenyl, 5-norbornene-2-yl, and 4-cyclooctenyl.

Examples where R$^1$ in formula (1) is substituted or unsubstituted aryl, are phenyl or unsubstituted naphthyl of which hydrogen may be optionally substituted with a halogen or C$_1$–C$_{10}$ alkyl. The halogen is preferably fluorine, chlorine, and bromine. In the C$_1$–C$_{10}$ alkyl, each hydrogen may be optionally substituted with fluorine and each —CH$_2$— group may be optionally replaced with —O—, —CH═CH— or phenylene. Therefore, preferred examples where R$^1$ in formula (1) is substituted or unsubstituted aryl include unsubstituted phenyl, unsubstituted naphthyl, alkyl phenyl, alkyloxyphenyl, alkenylphenyl, phenyl substituted with C$_1$–C$_{10}$ alkyl where one —CH$_2$— group is replaced with phenylene, and halogenated compounds thereof.

Examples of halogenated phenyl include pentafluorophenyl, 4-chlorophenyl, and 4-bromophenyl. Examples of alkylphenyl include 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl, and 2,4,6-tris(1-methylethyl)phenyl. Examples of alkyloxyphenyl include (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl, (4-octadecyloxy)phenyl, 4-(1-methylethoxy)phenyl, 4-(2-methylpropoxy)phenyl, and 4-(1,1-dimethylethoxy)phenyl. Examples of alkenylphenyl include 4-ethenylphenyl, 4-(1-methylethenyl)phenyl and 4-(3-butenyl)phenyl.

Examples of phenyl substituted with $C_1$–$C_{10}$ alkyl where —$CH_2$— group is optionally replaced with phenylene include 4-(2-phenylethenyl)phenyl, 4-phenoxyphenyl, 3-(phenylmethyl)phenyl, biphenyl, and terphenyl. 4-(2-phenylethenyl)phenyl is an example of ethylphenyl where one —$CH_2$— group of the ethyl group is replaced with phenylene and the other group is replaced with —CH═CH—.

Examples of phenyl of which benzene-ring hydrogens partially substituted with halogen and the others substituted with alkyl, alkyloxy or alkenyl include 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, and 2,3-difluoro-4-propoxyphenyl, 4-ethenyl-2,3,5,6-tetrafluorophenyl.

If $R^1$ in formula (1) is a substituted or unsubstituted arylalkyl, each hydrogen of the alkylene group may be optionally substituted with fluorine and each —$CH_2$— group may be optionally replaced with —O— or —CH═CH—. A preferred example of arylalkyl is phenylalkyl where the number of carbons should be preferably between 1 and 12, and more preferably between 1 and 8. Examples of phenylalkyl include phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl, and 1-phenylhexyl.

Each benzene-ring hydrogen of phenylalkyl may be optionally substituted with a halogen or $C_1$–$C_{12}$ alkyl where each hydrogen may be optionally substituted with fluorine and each —$CH_2$— group may be optionally replaced with —O—, —CH═CH—, cycloalkylene or phenylene. Examples of phenylalkyl substituted on the phenyl ring with fluorine include 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl and 2-(4-fluorophenyl)propyl.

Examples of phenylalkyl of which benzene-ring hydrogen is optionally substituted with chlorine include 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2-4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl, and 1-(4-chlorophenyl)butyl.

Examples of phenylalkyl of which benzene-ring hydrogen is optionally substituted with bromine include 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl, and 2-(4-bromophenyl)propyl.

Examples of phenylalkyl of which benzene-ring hydrogen is optionally substituted with $C_1$–$C_{12}$ alkyl include 2-methylphenylmethyl, 3-methylphenylmethyl, 4-methylphelylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)propyl, 2-(2,4-dimethylphenyl)propyl, 2-(3,4-dimethylphenyl)propyl, 2-(2,5-dimethylphenyl)butyl, (4-(1-methylethyl)phenyl)methyl, 2-(4-(1,1-dimethylethyl)phenyl)ethyl, 2-(4-(1-methylethyl)phenyl)propyl, and 2-(3-(1-methylethyl)phenyl)propyl.

Examples of phenylalkyl of which benzene-ring hydrogen is optionally substituted with fluorinated $C_1$–$C_{12}$ alkyl include 3-(trifluoromethyl)phenylmethyl, 2-(4-trifluoromethylphenyl)ethyl, 2-(4-nonafluorobutylphenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethylphenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexylphenyl)ethyl, 2-(4-heptadecafluorooctylphenyl)propyl, and 1-methyl-1-(4-heptadecafluorooctylphenyl)ethyl.

Examples of phenylalkyl of which benzene-ring hydrogen is optionally substituted with $C_1$–$C_{12}$ alkyl where one —$CH_2$— group is replaced with —CH═CH— include 2-(4-ethenylphenyl)ethyl, 1-(4-ethenylphenyl)ethyl, and 1-(2-(2-propenyl)phenyl)ethyl. Examples of phenylalkyl substituted on the phenyl ring by $C_1$–$C_{12}$ alkyl where one —$CH_2$— group is replaced by —O— include 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, 2-(3-(methoxymethyl)phenyl)ethyl and 3-(2-nonadecafluorodecenyloxyphenyl)propyl.

Examples of phenylalkyl of which benzene-ring hydrogen is optionally substituted with $C_1$–$C_{12}$ alkyl where one —$CH_2$— group is replaced with cycloalkylene and another —$CH_2$— group is optionally replaced with —O— include cyclopentylphenylmethyl, cyclopentyloxyphenylmethyl, cyclohexylphenylmethyl, cyclohexylphenylethyl, cyclohexylphenylpropyl and cyclohexyloxyphenylmethyl. Examples of phenylalkyl of which benzene-ring hydrogen is optionally substituted with $C_1$–$C_{12}$ alkyl where one —$CH_2$— group is replaced with phenylene another —$CH_2$— group is optionally replaced with —O— include 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl, and 2-(4-biphenylyl)propyl.

Examples of phenylalkyl where at least two of benzene-ring hydrogens are substituted with two different groups include 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmehtyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, (2,3,4,6-tetrachloro-5-methylphenyl)methyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl, and 11-(3-chloro-4-methoxyphenyl)undecyl.

The most preferable phenyls in phenylalkyl are unsubstituted phenyl and phenyl with at least one of the following substutuents: fluorine; $C_1$–$C_4$ alkyl; ethenyl; and methoxy.

Examples of phenylalkyl where one —$CH_2$— group of the alkylene is replaced with —O— or —CH=CH— include 3-phenoxypropyl, 1-phenylethenyl, 2-phenylethenyl, 3-phenyl-2-propenyl, 4-phenyl-4-pentenyl, and 13-phenyl-12-tridecenyl. Examples of phenylalkyl substituted on the phenyl ring by fluorine or methyl include 4-fluorophenylethenyl, 2,3-difluorophenylethenyl, 2,3,4,5,6-pentafluorophenylethenyl, and 4-methylphenylethenyl.

The most preferable examples of $R^1$ are $C_2$–$C_8$-alkyl(say, ethyl, isobutyl and isooctyl)-phenyl, halogenated phenyl, phenyl substituted with at least one methyl group, methoxyphenyl, naphthyl, phenylmethyl, phenylethyl, phenylbutyl, 2-phenylpropyl, 1-methyl-2-phenylethyl, pentafluorophenylpropyl, 4-ethylpheylethyl, 3-ethylphenylethyl, 4-(1,1-dimethylethyl)phenylethyl, 4-ethenylphenylethyl, 1-(4-ethenylphenyl)ethyl, 4-methoxyphenylpropyl, and phenoxypropyl.

$A^2$ is preferably a hydroxyl-terminal organic groups represented by formula (3) or (5).

Then, the functional group represented by formula (3) is explained particularly.

H—O-$Z^1$-             (3)

Referring to $Z^1$ in formula (3), preferable examples is $C_1$–$C_{22}$ alkylene or $C_3$–$C_8$ alkenylene, and its specific example is a group in formulas (13) to (29). More preferably, $Z^1$ is $C_1$–$C_{22}$ alkylene, and its specific example is a group in formulas (13) to (25). The most preferable example of $Z^1$ is $C_1$–$C_6$ straight-chained alkylene, and its specific example is a group in formula (13), (14), (15), (22) and (23). In the alkylene alkenylene groups, each —$CH_2$— group may be optionally replaced with —O—.

H—O—(CH$_2$)$_2$—             (13)

H—O—(CH$_2$)$_3$—             (14)

H—O—(CH$_2$)$_5$—             (15)

H—O—(CH$_2$)$_{10}$—             (16)

H—O—(CH$_2$)$_{11}$—             (17)

H—O—(CH$_2$)$_{15}$—             (18)

H—O—(CH$_2$)$_{22}$—             (19)

(20)

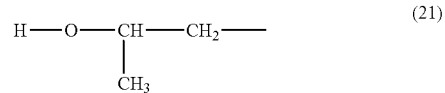
(21)

H—O—(CH$_2$)$_2$—O—(CH$_2$)$_2$—             (22)

H—O—(CH$_2$)$_2$—O—(CH$_2$)$_3$—             (23)

H—O—(CH$_2$)$_2$—O—(CH$_2$)$_4$—             (24)

H—O—(CH$_2$)$_2$—O—(CH$_2$)$_5$—             (25)

H—O—CH$_2$—CH=CH—             (26)

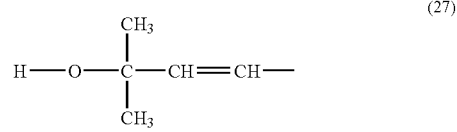
(27)

H—O—CH$_2$—CH=CH—(CH$_2$)$_5$—             (28)

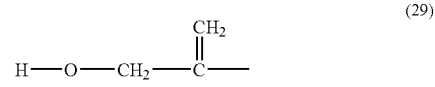
(29)

Then, the functional group represented by formula (5) is explained particularly.

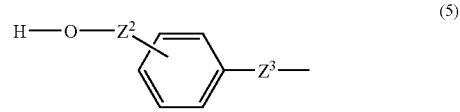
(5)

Referring to the group in formula (5), preferably, $Z^2$ is a single bond or $C_1$–$C_3$ alkylene, and $Z^3$ is $C_1$–$C_{22}$ alkylene or $C_3$–$C_8$ alkenylene, and their specific examples are groups in formulas (30) to (37). More preferably, $Z^2$ is a single bond or $C_1$–$C_3$ alkylene, and $Z^3$ is $C_1$–$C_{22}$ alkylene. In the most preferred example, $Z^2$ is a single bond or —$CH_2$—, and $Z^3$ is —$C_2H_4$—, and their specific examples are groups in formulas (30) and (34). Each —$CH_2$— of the alkylene or alkenylene groups may be optionally replaced with —O—, and $Z^2$ can be bound to the benzene ring at any carbon position.

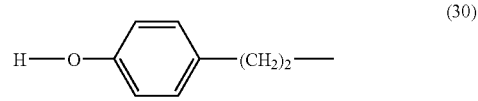
(30)

-continued

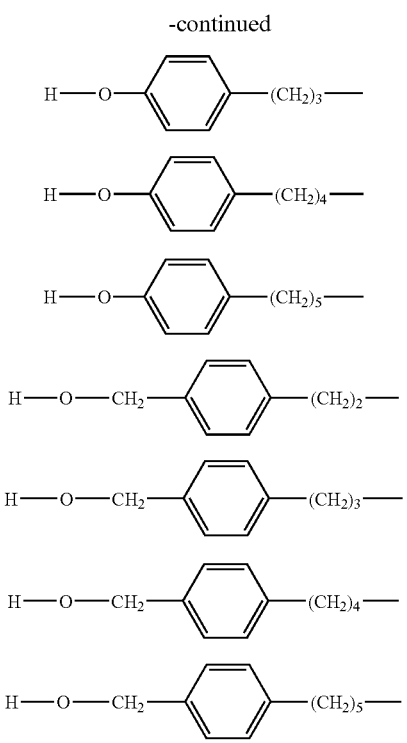

(31)
(32)
(33)
(34)
(35)
(36)
(37)

Then, the production process for the silicon compound of the present invention is explained. One of a preferable raw material of the present invention is a silicon compound represented by formula (2),

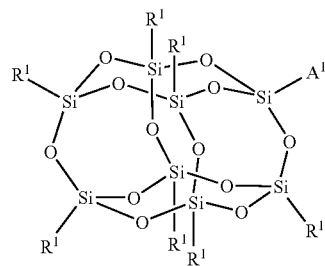

(2)

Wherein: in formula (2), $R^1$ is the same as $R^1$ in formula (1), and $A^1$ is preferably an organic group that has an acyloxy group represented by formula (4) or (6).

Then, the functional group represented by formula (4) is explained particularly.

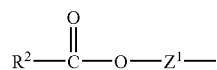

(4)

Referring to formula (4), preferably, $R^2$ is selected from the group consisting of $C_1$–$C_{17}$ alkyl, $C_2$–$C_3$ alkenyl, substituted or unsubstituted phenyl, and unsubstituted phenylalkyl, and $Z^1$ is $C_1$–$C_{22}$ alkylene or $C_3$–$C_8$ alkenylene, and their specific examples are groups in formulas (38) to (78). More preferably, $Z^1$ is $C_1$–$C_{22}$ alkylene, and $R^2$ is either $C_1$–$C_{17}$ alkyl or $C_2$–$C_3$ alkenyl, and their specific examples are groups in formulas (38) to (55), (61) to (64) and (69) to (78). Most preferably, $Z^1$ is straight-chained $C_1$–$C_6$ alkylene, and $R^2$ is a methyl group, and their specific examples are groups in formulas (33), (34), (38) or (39). Each hydrogen of the alkyl groups is optionally substituted with fluorine. Each —$CH_2$— group of the alkylene or alkenylene groups may be optionally replaced with —O—.

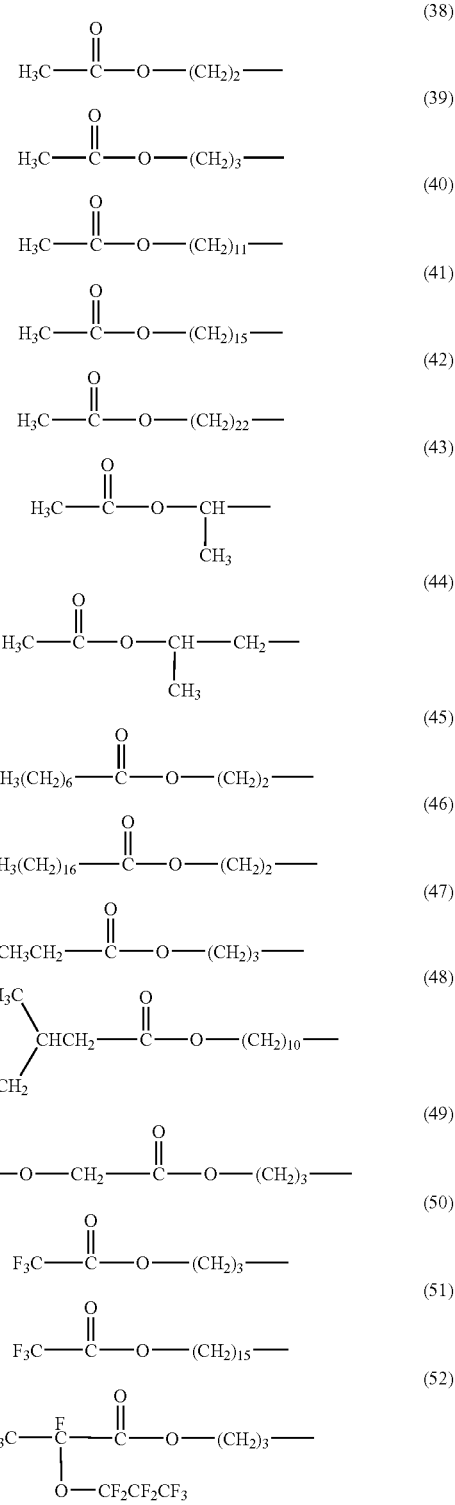

(38)
(39)
(40)
(41)
(42)
(43)
(44)
(45)
(46)
(47)
(48)
(49)
(50)
(51)
(52)

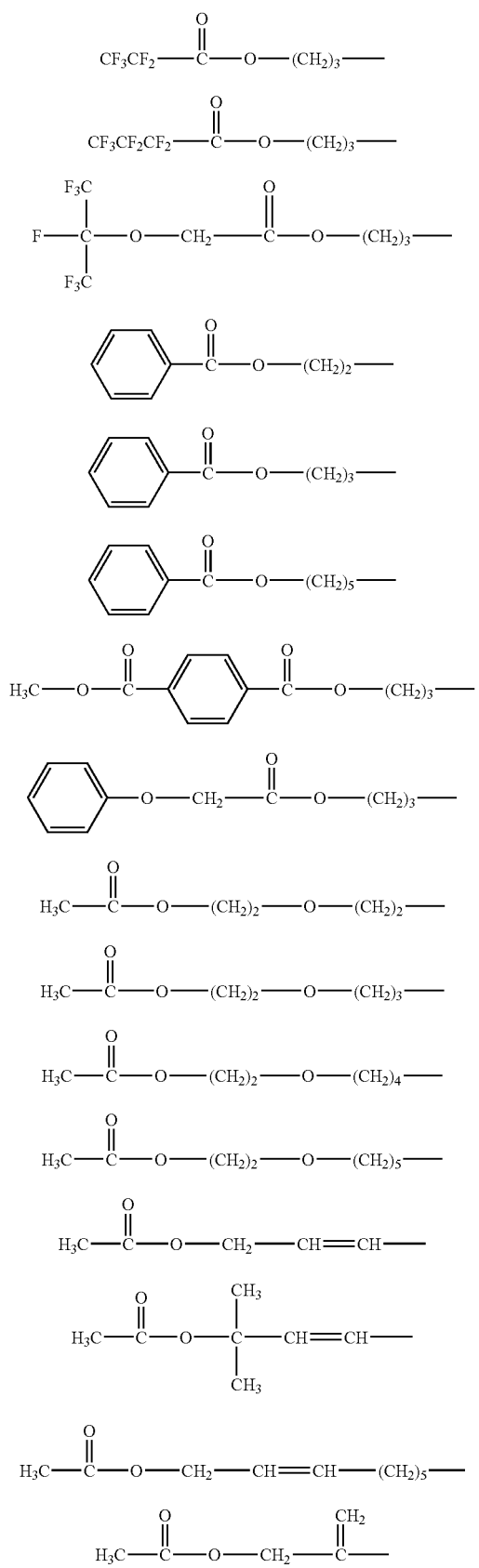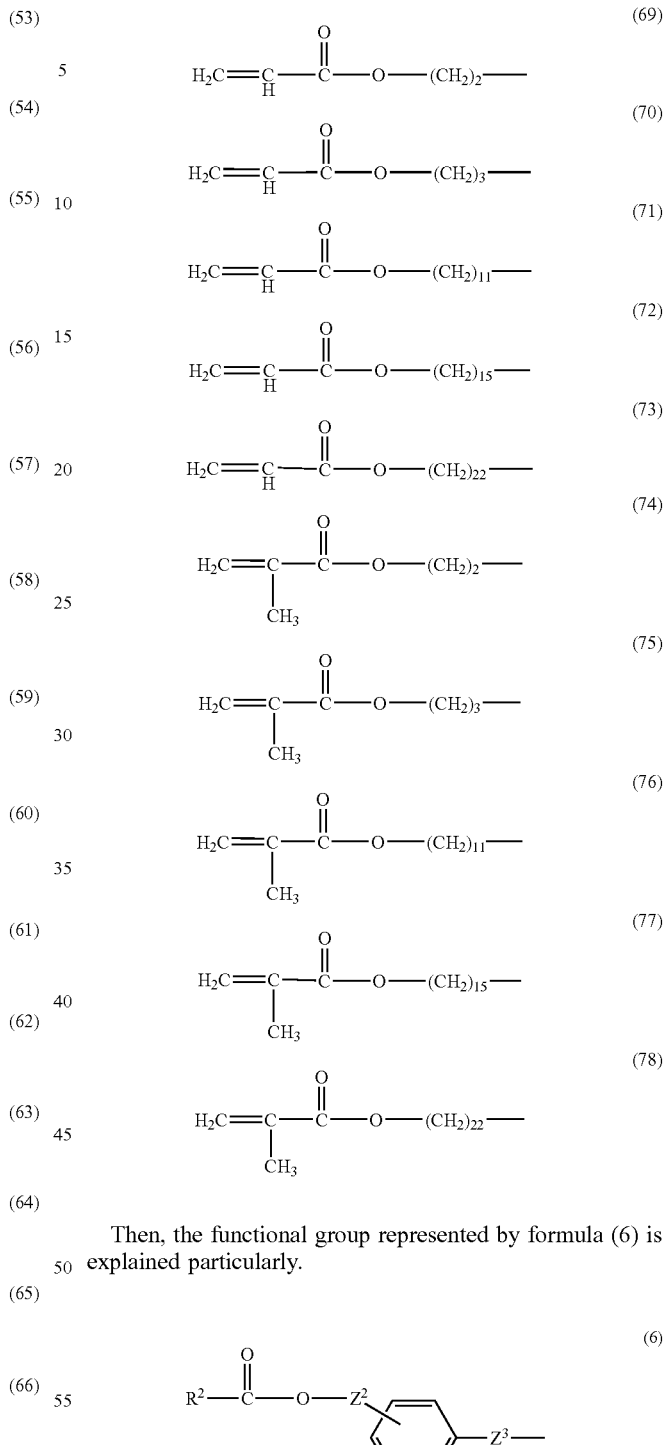

Then, the functional group represented by formula (6) is explained particularly.

Referring to formula (6), preferably, $R^2$ is selected from the group consisting of $C_1$–$C_{17}$ alkyl, $C_2$–$C_3$ alkenyl, substituted or unsubstituted phenyl, unsubstituted phenylalkyl, $Z^2$ is either a single bond or $C_1$–$C_3$ alkylene, and $Z^3$ is either $C_1$–$C_{22}$ alkylene or $C_3$–$C_8$ alkenylene, and their specific examples are formulas (79) to (102). More preferably, $R^2$ is either $C_1$–$C_{17}$ alkyl or $C_2$–$C_3$ alkenyl, $Z^2$ is either a single bond or $C_1$–$C_3$ alkylene, and $Z^3$ is $C_1$–$C_{22}$ alkylene. Most preferably, $R^2$ is methyl, $Z^2$ is either a single bond or —$CH_2$—, and $Z^3$ is —$C_2H_4$—, and their specific examples are formulas (79) and (83). Each —$CH_2$— group of the alkylene and alkenylene groups may be optionally replaced with —O—. $Z^2$ can be bound to the benzene ring at any carbon position.

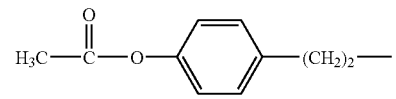 (79)

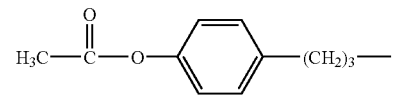 (80)

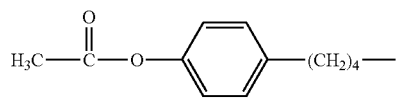 (81)

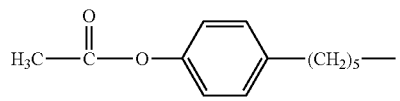 (82)

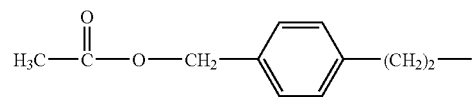 (83)

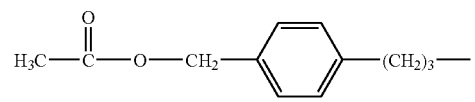 (84)

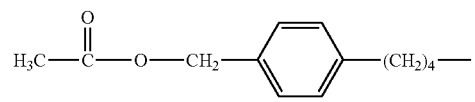 (85)

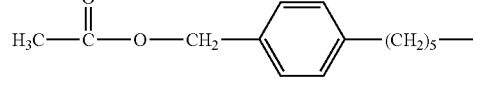 (86)

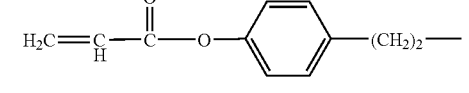 (87)

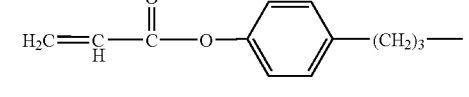 (88)

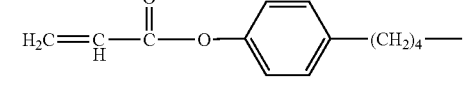 (89)

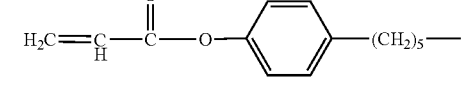 (90)

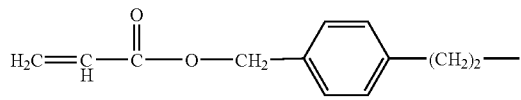 (91)

-continued

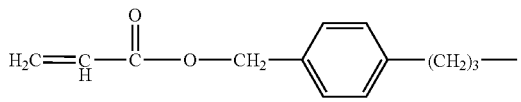 (92)

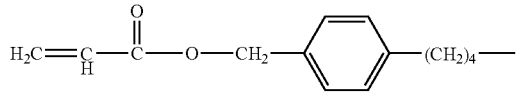 (93)

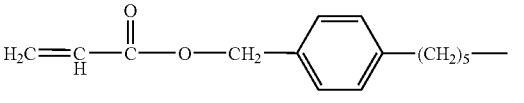 (94)

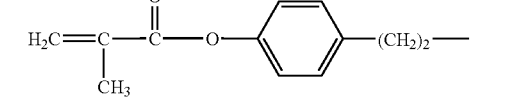 (95)

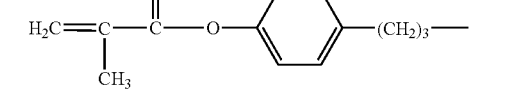 (96)

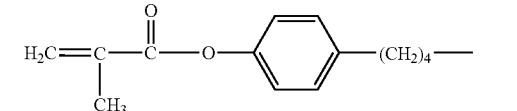 (97)

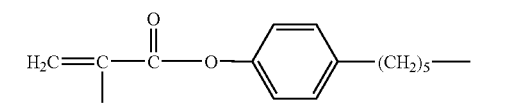 (98)

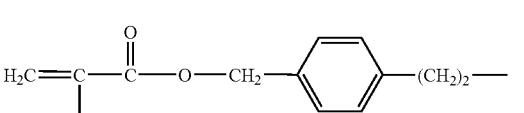 (99)

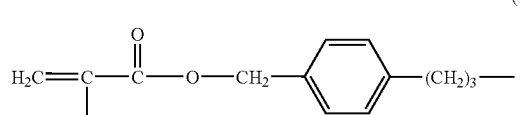 (100)

 (101)

 (102)

Then, the production process for the present invention is explained. A preferable raw material of a silicon compound represented by formula (2) is a silicon compound (silsesquioxane compound) that has a silanol group represented by formula (7).

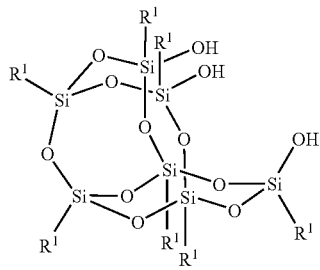

(7)

R[1] in formula (7) is the same as R[1] in formula (2). Such a compound can be prepared through hydrolysis and maturation of chlorosilane. For example, Frank J. Feher et al have prepared a compound in formula (7) with R[1] being cyclopentyl by reacting cyclopentyltrichlorosilane in water-acetone mixed solvent at room temperature or reflux temperature, and maturing for two weeks (Organometallics, 10, 2526-(1991), and Chemical European Journal, 3, No. 6, 900-(1997)). A compound (2) can be prepared by reacting a compound (7) with trichlorosilane having an acyloxy group by utilizing the reactivity of silanol (Si—OH). Preferable trichlorosilane which has an acyloxy group is a compound (8) or (9).

A compound (10) can be prepared by reacting a compound (7) with a compound (8).

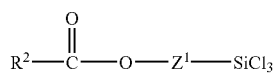

(8)

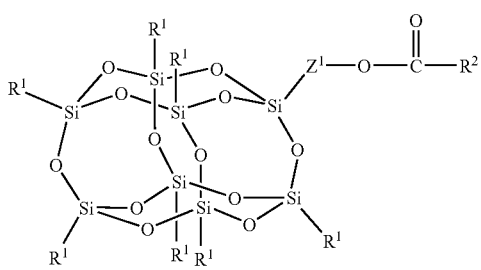

(10)

In consideration of using a commercially available compound (7), a preferable example of R[1] in formula (7) is selected from a group consisting of: $C_1$–$C_8$ alkyl wherein each hydrogen may be optionally substituted with fluorine and each —$CH_2$— group may be optionally replaced with —O—, —CH=CH—, cycloalkylene or cycloalkenylene; phenyl wherein each hydrogen may be optionally substituted with halogen, methyl or methoxy; unsubstituted naphthyl; and phenylalkyl wherein each hydrogen atom in a benzene ring may be optionally substituted with fluorine, $C_1$–$C_4$ alkyl, ethenyl or methoxy and each —$CH_2$— group may be optionally replaced with —O—, and other characters in formulas (8) and (10) are the same as defined above.

A compound (11) can be obtained by reacting a compound (7) with a compound (9).

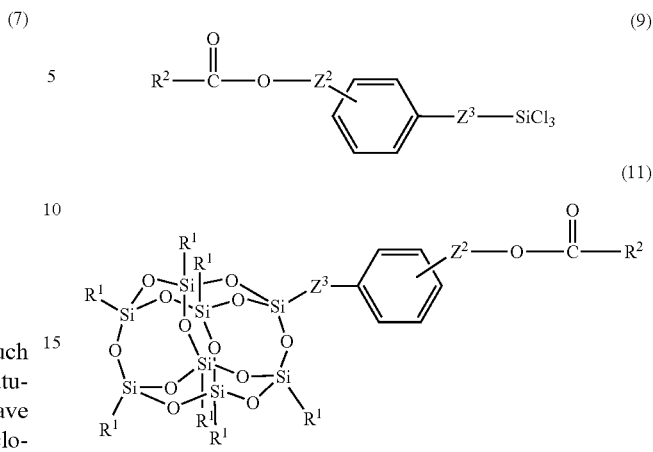

Preferable examples of R[1] in formula (7) are the same as defined above. The other symbols of formula (9) and (11) are as defined above. The binding position of $Z^2$ is as defined above.

A compound (2) can be prepared from compounds (7) and (8) or compounds (7) and (9) through the "Corner-capping reaction," a reaction utilizing what is called nucleophilic substitution as described in, for example, Macromolecules, 28, 8435-(1995).

The selection conditions for solvents used in the above-described nucleophilic substitution reaction are as follows: they do not react with compounds (7) and (8) or compounds (7) and (9); and they are sufficiently dehydrated. Examples of these solvents include tetrahydrofuran, toluene, and dimethylformamide and so on, and the most preferable solvent is sufficiently dehydrated tetrahydrofuran. In consideration of full reaction of Si—OH (silanol) group of the compound (7), the preferable equivalent ratio of the compound (8) or (9) to the Si—OH (silanol) group of the compound (7) is 1 to 5. Because hydrochloride is generated through the reaction of the hydrogen of silanol and the chlorine of the chlorosilan, it must be removed from the reaction system. Although there is no limitation on the removing method of hydrochloride,; various organic bases are preferably used. Though, any bases may be used as long as they allow the inhibition of side reactions and the smooth progress of the main reaction, for example, pyridine, dimethylaniline, triethylamine, triethylamine, and tetramethylurea are indicated, and most preferable organic base is triethylamine. The equivalent ratio of triethylamine to the Si—OH group of a compound (7) is preferably 3 to 5. Reaction temperature is that at which quantitative nucleophilic substitution reactions occur without side reactions. Raw materials can be prepared at low temperature, and most preferably, say, in an ice bath. The downstream procedures can be operated at room temperature. No particular restriction is imposed on the reaction time; any time may be used as long as enough quantitative nucleophilic reactions proceed. Usually, the silicon compound (2) is obtained for a reaction time of 13 hours.

Another preferable raw material employed in the invention is a silsesquioxane compound represented by formula (12).

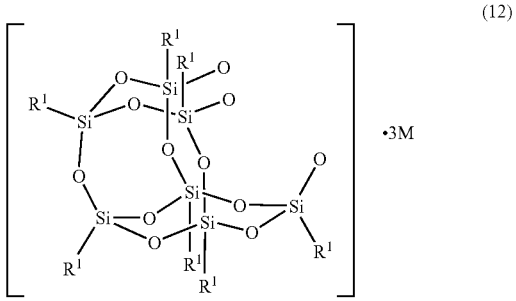

(12)

The compound (12) can be prepared by the steps of: hydrolysis of a silane compound having trifunctional hydrolyzable groups to obtain a silsesquioxane oligomer; and reaction of the oligomer with a monovalent alkali-metal hydroxide in an organic solvent. The compound (12) can also be prepared through hydrolysis and condensation of a silane compound having trifunctional hydrolysable groups in the presence of water and a monovalent alkali-metal hydroxide. Using both methods, the compound (12) can be prepared for a shot with a high yield (see, for example, Pat. No. PCT/JP02/04776). Because the compound (12) has a higher reactivity than the silanol groups of compound (7), its derivatives can easily be prepared from it with a high yield. In addition, the compound (12) has —ONa groups as its reactive groups, so reaction procedures are easy and reaction can be finished completely. That is, a compound (1) can easily be prepared from a compound (12) and trichlorosilane having an acyloxy group.

It is also preferable, that a compound (10) is prepared by reacting said compound (8), in case of utilizing a compound (12). $R^1$ in formula (12) is the same as $R^1$ in formula (1), and its preferable examples are as described for formula (7). M in formula (12) is a monovalent alkali metal atom, preferably sodium or potassium, and most preferably sodium. A compound (10) can be prepared by reacting a compound (12) with a compound (8) according to the method using a compound (7). The equivalent ratio of the compound (8) to the Si—ONa group of the compound (12) should preferably range from 1 to 5. Although this reaction requires no organic bases to remove hydrochloride, they may be used as catalysts to permit a smooth reaction progress. Organic bases that allow the inhibition of side reactions and smooth progress of the main reaction include, though not restricted specifically, for example, pyridine, dimethylaniline, triethylamine, and tetramethylurea, and more preferably, triethylamine. The equivalent ratio of triethylamine to the Si—ONa group of the compound (12) should preferably range from 3 to 5. Solvents, reaction temperature and reaction times are as defined for the reaction using a compound (7). A compound (11) can be prepared by reacting the compound (12) with said compound (9) according to the method for preparing a compound (10) from a compound (8).

If a distillation method is used to remove unreacted raw materials or solvents (both of which may be referred to as impurities hereinafter), the main resulting product is maintained at a high temperature for a prolonged period of time, which may lead to decomposition. Preferably, purification through recrystallization or the extraction of impurities with organic solvents would be used to efficiently remove impurities without a significant reduction in purity of the compounds (10) and (11). Using the compound (10) as an example, the purification method through recrystallization is explained particularly. This purification is performed as follows: first, the impurities containing substance is first dissolved in a solvent, with a preferable concentration of 1 to 15 percent by weight. The solution is transferred into concentration equipment, such as a rotary evaporator, and concentrated under reduced pressure until precipitation of a crystal has been initiated. The mixture is then maintained at atmospheric pressure and room or low temperature, and filtrated through a filter or centrifugally separated to separate the crystallized solid and the solvent containing impurities. The solvent also includes some of the crystal, and the above-described procedures may be repeated to increase the yield of the compound (10). The same applies to the process for removing impurities in the compound (11).

The selection condition of preferable solvents used for recrystallization is; it does not react with the compound (10), it dissolves the compound and impurities completely before condensation, it dissolves only the impurities and crystallize the compound with high efficiency during condensation, and it has relatively low boiling point, and so on. Examples of preferable solvents meeting these conditions are esters and aromatics, and the most preferably solvents are ethyl acetate and toluene. In addition, a higher purity can be achieved through large repeat number of the recrystallization procedure. The same conditions for selecting solvents apply to recrystallization of the compound (11).

Using the compound (10) as an example, the method for extracting impurities with an organic solvent is explained particularly. This extraction method is performed as follows: first, the compound (10) containing impurities is transferred into an organic solvent that dissolves only the impurities. The mixture is stirred to extract only the impurities, and the remaining solid is isolated through filtration or centrifugal separation. So long as organic solvents dissolve the impurities and not the compound (10), they are not restricted specifically, however,alcohols such as methanol, ethanol, and isopropylalcohol, and aromatic hydrocarbons such as toluene and xylene are preferred. No particular restriction is imposed on the extraction time; any length of time may be used in order to ensure efficient removal of impurities, and preferably in the range of 1 to 5 hours. No restriction is imposed on the extraction temperature; any temperature may be used in order to ensure efficient removal of impurities, and preferably 10 to 150° C., more preferably, 10 to 50° C. and most preferably 10 to 40° C. A higher purity can be achieved through repetition of the impurity extraction procedure using an organic solvent.

Then, the preparing method of compound (1) from the compound (2) through hydrolysis or transesterification in the presence of an acid or basic catalyst is explained. For this object, the method as described on pp. 150 to 157 of "Protection for the Hydroxyl Group, Including 1,2-and 1,3-Diols. In PROTECTIVE GROUPS IN ORGANIC SYNTHESIS —$3^{rd}$ Ed.; T. W. Greene and P. G. M. Wuts Eds; John Wiley & Sons, Inc. 1999." can be adopted. Said literature states on pp. 712 to 713 that the reaction proceeds under both acidic and basic conditions.

In transesterification or hydrolysis using a compound (2), preferably, the compound (2) is dissolved evenly or the main product (1) is dissolved according to the reaction progress. Specifically, in transesterification or hydrolysis using a compound (10) or (11), more preferably, the compound (2) is dissolved evenly or a silsesquioxane compound having hydroxyl groups prepared from each raw material is evenly dissolved according to the reaction progress. Solvents in which the above-described reaction proceeds efficiently are, though not restricted specifically, alcohols, more preferably ethanol and methanol, and most preferably, methanol.

It is preferable that transesterification or hydrolysis is conducted using a regulator that does not inhibit these reactions and is able to dissolve the compound (2). The regulator should be a solvent. Examples of the solvent include, though not restricted specifically, hydrochlorofluorocarbon solvents (HCFC-141b and HCFC-225), hydrofluorocarbon (HFCs) solvents (HFCs of at least two carbons), perfluorocarbon solvents (perfluoropentane and perfluorohexane), alicyclic hydrofluorocarbon solvents (fluorocyclopentane and fluorocyclobutane), oxygen-containing fluorinated solvents (fluoroether, fluoropolyether, fluoroketone, and fluoroalcohol), chloroform, methylenechloride and orthodichlorobenzne.

No particular restriction is imposed on the ratio of a regulator to an alcohol; any ratio may be used so long as quantitative transesterification or hydrolysis proceeds. For example, in a chloroform/methanol solvent, the ratio, chloroform/methanol (volume ratio), should be preferably 1/1, 2/3 or 3/2, and most preferably 1/1.

No particular restriction is imposed on the reaction temperature; any temperature may be used so long as quantitative transesterification or hydrolysis proceeds without any side reactions: a preferred range is 0 to 100° C., and more preferably 20 to 40° C. No particular restriction is imposed on the reaction time; any time may be used in order to ensure that quantitative transesterification or hydrolysis proceeds. Usually, the desired silicon compound is obtained during 24 to 100 hours.

No particular restriction is imposed on the type of acidic or basic catalyst employed in the invention; any catalyst may be used so long as quantitative transesterification or hydrolysis proceeds. Examples of the catalyst include critic acid monohydrate, sodium hydrogen-carbonate, potassium carbonate, potassium prussiate, guanidine, ammonia, $BF_3$, $HBF_4$, p-toluene sulfonate, hydrochloric acid and sulfuric acid, and most preferably sulfuric acid. No particular restriction is imposed on the catalyst content of a solvent. For example, in a chloroform/methanol/sulfonic acid solvent, the sulfuric acid content of the solvent should be preferably in the range of 0.1 to 5 percent by weight, more preferably 0.1 to 1.0 percent by weight, or most preferably 0.1 to 0.5 percent by weight.

Therefore, as the production process for silsesquioxane having hydroxyl groups from a compound (10) or (11), the method of transesterification using a chloroform/methanol/sulfonic acid solvent is most preferable, though not restricted to it. The silsesquioxane compound having hydroxyl groups thus obtained is purified by said purification method through recrystallization and said extraction method of impurities using an organic solvent.

EXAMPLES

Hereinafter, the invention is further explained by means of a series of examples, however,which do not limit the scope of the invention.

The following is a list of symbols used in the invention and their meanings.

Ph: Phenyl
Ch: Cyclohexyl
Cp: Cyclopentyl
Et: Ethyl
iBu: Isobutyl
iOc: Isooctyl
TFPr: Trifluoropropyl
TDFOc: Tridecafluoro-1,1,2,2-tetrahydrooctyl
TMS: Trimethylsilyl
Mn: Number-average molecular weight
Mw: Weight-average molecular weight

Example 1

Preparation of Polyphenylsilsesquioxane (Compound A)

Ice water (640.7 g) and toluene (200 g) were placed into a 2-litter four-necked separable flask equipped with a stirrer, a reflux condenser, a thermometer and a dropping funnel, and then lowered the inside temperature to 0° C. with stirring. A mixture of phenyltrichlorosilane (211.5 g) and toluene (130 g) dehydrated overnight with molecular sieves was transferred into the dropping funnel and added dropwise for one hour at the rate to prevent the internal temperature of the flask not to exceed 2° C. After the contents was stirred at room temperature for 30 minutes, the resulting product was washed with purified water. Toluene was removed under reduced pressure to obtain a solid compound A (120.7 g) with a weight-average molecular weight of approximately 3100.

Preparation of Sodium-bond Phenylsilsesquioxane Compound (Compound B)

The compound A obtained above (12.9 g), tetrahydrofuran dehydrated overnight with molecular sieves (250 mL), and sodium hydroxide (4.0 g) were placed into a 500-mL four-necked flask equipped with a reflux condenser and a thermometer. The mixture was stirred and heated at 67° C. under reflux. After four hours of reflux, a minute amount of powder was precipitated and the solution began to exhibit a white turbidity. After another hours of reflux, the reaction was completed. The precipitate was washed with tetrahydrofuran, filtered and dried under vacuum to obtain a compound B (10.1 g).

Example 2

Introduction of Trimethylsilyl Groups into a Compound B (Compound C)

The compound B prepared in example 1 (2.0 g), toluene (100 g), triethylamine (1.7 g) and trimethylchlorosilane (1.4 g) were placed to a 200-ml four-necked flask equipped with a reflux condenser, and stirred with a magnetic stirrer at room temperature for two hours. After the reaction was completed, the resulting product was washed with purified water and dried under vacuum to obtain a compound C (2.1 g).

The structure of compound C was analyzed by $^1$H-NMR, $^{13}$C-NMR, $^{29}$Si-NMR, mass spectroscopy, X-ray and IR The $^1$H-NMR and $^{13}$C-NMR data revealed the integral ratio of phenyl groups to trimethylsilyl was 7:3. The $^{29}$Si-NMR data revealed a single peak which suggested trimethylsilyl groups at 11.547 ppm, and three peaks that suggested a T-structure containing a phenyl group at −77.574 ppm, −78.137 ppm, and −78.424 ppm (relative to trimethylsilane) with an integral ratio of 1:3:3. The mass spectroscopy spectrum revealed that the absolute molecular weight matched with the theoretical value of the structure of formula (103). The X-ray crystal structure analysis found that the resulting compound C exhibited the structure of formula (103). The IR spectrum found an absorption band assigned to Si—Ph bending vibration at 1430 and 1590 cm$^{-1}$, an absorption band assigned to harmonic of a substituted benzene ring at 1960 to 1760 cm$^{-1}$, an absorption band assigned to Si—O—Si stretching vibration at 1200 to 950 cm$^{-1}$, and an absorption band assigned to Si—CH$_3$ vibration at 1250 cm$^{-1}$. These results corroborate the formation of a compound substituted with trimethylsilyl groups (compound C) with a structure of formula (103) and suggests that the sodium-bound phenylsilsesquioxane compound obtained (compound B) has a structure of formula (104). The T-structure means a structure where three oxygen atoms are bound to an Si atom.

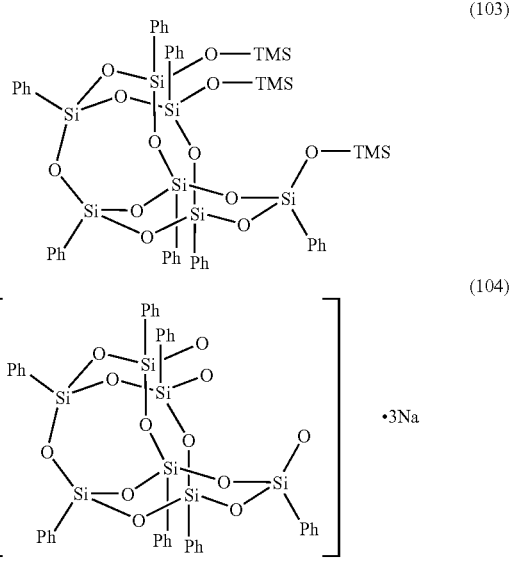

Example 3

Preparation of Sodium-bound Phenylsilsesquioxane Compound (Compound B) from Phenyltrimethoxysilane Phenyltrimethoxysilane (99 g), sodium hydroxide (10 g) and 2-propanol (500 ml) were placed into a 1-L four-necked flask equipped with a stirrer bar, a reflux condenser, a thermometer, and a dropping funnel. The mixture was stirred with a magnetic stirrer at room temperature and deionized water (11 g) was added dropwise from the dropping funnel over two minutes. The flask was heated in an oil bath to the refluxing temperature of 2-propanol. After 1.5 hours of reflux, the reaction was completed. The flask was removed from the oil bath and allowed to stand at room temperature overnight to fully crystallize the precipitate. The crystallized solid was filtered though a 0.1-μm membrane filer using a pressure filtration equipment. The solid obtained was washed once with 2-propanol, and dried under reduced pressure at 70° C. for four hours to obtain a white solid (compound B, 66 g).

Example 4

Introduction of Trimethyl Groups into a Compound B Prepared from Phenyltrimethoxysilane (Compound C)

The compound B prepared in Example 3 (1.2 g), tetrahydrofuran (12 g), and triethylamine (1.8 g) were placed into a 50-mL four-necked flask equipped a stirrer bar, with a dropping funnel, a reflux condenser and a thermometer. The apparatus was purged with dry nitrogen and sealed. The reactants were stirred with the magnetic stirrer and chlorotrimethylsilane (2.3 g) was added dropwise from the dropping funnel at room temperature over approximately one minute. After completion of the addition, the content was stirred for another three hours to complete the reaction. Pure water (10 g) was added to hydrolyze the resulting sodium chloride and unreacted chlorotrimethylsilane. The resulting mixture was transferred into a separating flask and the water layer was removed. The organic layer remaining inside was repeatedly washed with deionized water until the washing water became neutral. The organic layer obtained was dehydrated with magnesium sulfate anhydride. The desiccant was removed by filtration, and the filtrate was concentrated under reduced pressure with a rotary evaporator to obtain a white solid (compound C, 1.2 g).

The structure of the compound C was analyzed by $^1$H-NMR, $^{13}$C-NMR, $^{29}$Si-NMR, mass spectroscopy, X-ray and IR. $^1$H-NMR and $^{13}$C-NMR data revealed the integral ratio of phenyl groups to trimethylsilyl groups was 7:3. The $^{29}$Si-NMR data revealed a peak that suggested trimethyl groups at 11.547 ppm, and three peaks that suggested a T-structure containing a phenyl group at −77.574 ppm, −78.137 ppm, and −78.424 ppm (relative to trimethylsilane) in an integral ratio of 1:3:3. The mass spectroscopy spectrum showed that the absolute molecular weight matched with the theoretical value of the structure of said formula (103). The X-ray crystal structure analysis found that the compound C had the structure of said formula (103). The IR analysis found an absorption band assigned to Si—Ph bending vibration at 1430 and 1590 cm$^{-1}$, an absorption band assigned to harmonic of a substituted benzene ring at 1960 to 1760 cm$^{-1}$, an absorption band assigned to Si—O—Si stretching vibration at 1200 to 950 cm$^{-1}$, and an absorption band assigned to Si—CH$_3$ at 1250 cm$^{-1}$. These analytical results corroborate formation of a compound prepared through the substitution of trimethylsilyl groups (compound C) with the structure of said formula (103) and suggests that the resulting sodium-bound phenylsilsesquioxane compound (compound B) has the structure of said formula (104). The T-structure means a structure where three oxygen atoms are bound to a Si atom.

Example 5

Preparation of a Sodium-bound Cyclohexylsilsesquioxane Compound from Cyclohexyltrimethoxysilane A sodium-bound cyclohexylsilsesquioxane compound represented by formula (105) can be prepared as in Example 3 except that in place of phenyltrimethoxysilane, cyclohexyltrimethoxysilane is used.

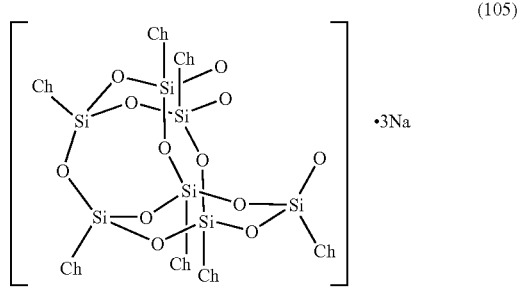
(105)

Example 6

Introduction of Trimethylsilyl Groups into a Compound (105)

A silsesquioxane compound of formula (106) having trimethylsilyl groups can be prepared as in Example 4 except that in place of compound (104), a compound (105) is used. The production of said compound (105) can be verified through the structural analysis of a compound (106) as in Example 4.

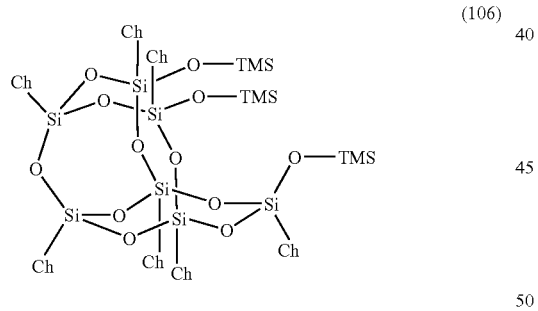
(106)

Example 7

Preparation of a Sodium-bound Cyclopentylsilsesquioxane Compound from Cyclopentyltrimethoxysilane Cyclopentyltrimethylsilane (19.0 g), tetrahydrofran (THF) (100 mL), sodium hydroxide (1.7 g), and deionized water (2.3 g) were placed into a 200-mL four-necked flask equipped with a reflux condenser, a thermometer and a dropping funnel. The reactants were stirred with a magnetic stirrer and the flask was heated in an oil bath to the refluxing temperature of 67° C. After ten hours of reflux with stirring, the reaction was completed. The flask was removed from the oil bath and allowed to stand at room temperature overnight to fully crystallize the precipitate. The resulting solid was filtered off and dried under vacuum to obtain a powder solid (4.2 g).

Example 8

Introduction of Trimethylsilane Groups

The compound prepared in example 7 (1.0 g), tetrahydrofuran (30 mL), triethylamine (0.5 g), and trimethylchlorosilane (0.7 g) were placed into a 100-mL four-necked flask equipped with a reflux condenser. The reactants were stirred with a magnetic stirrer at room temperature for two hours. After the reaction was completed, treatment procedures were applied as in example 4, and a powdery solid (0.9 g) was obtained.

The structure of the resulting product was analyzed by $^1$H-NMR, $^{29}$Si-NMR and X-ray. The $^1$H-NMR data revealed the integral ratio of cyclopentyl groups to trimethyl groups was 7:3. The $^{29}$Si-NMR data revealed a peak that suggested trimethyl groups at 8.43 ppm, and three peaks that suggested a T-structure containing cyclopentyl groups at −66.37 ppm, −67.97 ppm and −67.99 ppm. The ratio of the intensity of a sum of the −67.97 ppm and −67.99 ppm peaks to that of the −66.37 ppm peak was 6:1. These results combined with the crystal structure obtained through X-ray analysis indicate that the compounds of the powdery solid are of the silicon compound represented by formula (107). This suggests that the compound obtained in example 7 has the structure represented by formula (108).

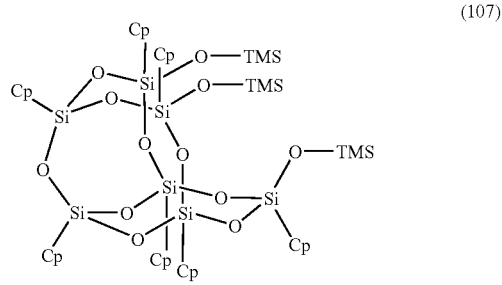
(107)

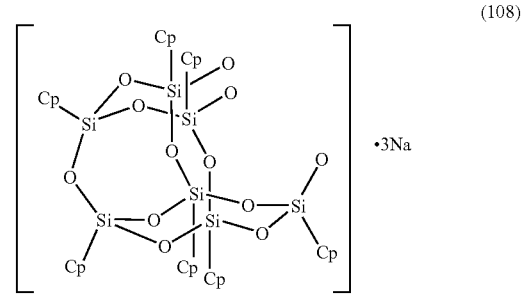
(108)

Example 9

Preparation of a Sodium-bound Ethylsilsesquioxane Compound from Ethyltrimethoxysilane A sodium-bound ethylsilsesquioxane compound represented by formula (109) can be prepared as in example 3 except that in place of phenyltrimethoxysilane, ethyltrimethoxysilane is used.

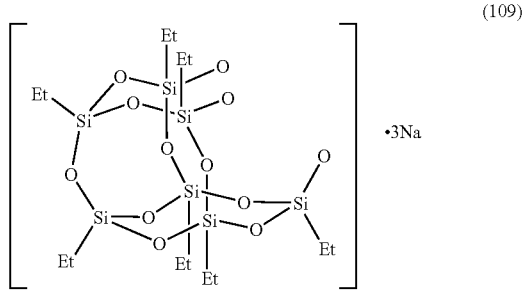

(109)

Example 10

Introduction of Trimethylsilyl Groups into a Compound (109)

An ethylsilsesquioxane compound represented by formula (110) can be prepared as in example 4 except that in place of compound (104), a compound (109) is used. The production of said compound (109) can be verified by conducting structure analyses of the compound (110) as in example 4.

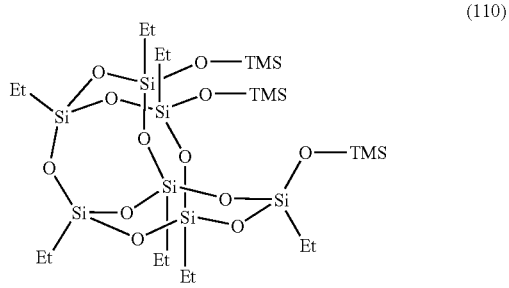

(110)

Example 11

Preparation of a Sodium-bound Isobutylsilsesquioxane Compound from Isobutyltrimethoxysilane Isobutyltrimethoxysilane (18.7 g), tetrahydrofuran (100 mL), sodium hydroxide (1.8 g) and deionized water (2.4 g) were placed into a 200-mL four-necked flask equipped with a reflux condenser, a thermometer, and a dropping funnel. The reactants were stirred and heated to the refluxing temperature of 67° C. After ten hours of reflux with stirring, the reaction was completed. The resulting liquid was concentrated at constant pressure until precipitation of a solid had just been initiated. The resulting product was allowed to stand at room temperature overnight to fully precipitate the solid. The solid obtained was filtered off and then dried under vacuum to obtain a powdery solid (5.1 g).

Example 12

Introduction of Trimethylsilyl Groups

The powdery solid prepared in example 11 (1.0 g), tetrahydrofuran (20 mL), triethylamine (0.5 g) and trimethylsilane (0.8 g) were placed into a 200-mL four-necked flask equipped with a reflux condenser. The reactants were stirred with a magnetic stirrer at room temperature for two hours. After the reaction was completed, treatment procedures were applied as in example 4 to obtain a powdery solid (0.9 g).

The structure of the powdery product was analyzed by $^1$H-NMR and $^{29}$Si-NMR The $^1$H-NMR data revealed the integral ratio of isobutyl groups to trimethylsilyl groups to be 7:3. The $^{29}$Si-NMR data revealed a peak that suggested trimethylsilyl groups at 8.72 ppm and three peaks that suggested a T-structure containing isobutyl groups at −67.38 ppm, −68.01 ppm and −68.37 ppm at an integral ratio of 1:3:3. These results indicate that the powdery compound is of the silicon compound represented by formula (111) and suggests that the compound prepared in example 11 has the structure represented by formula (112).

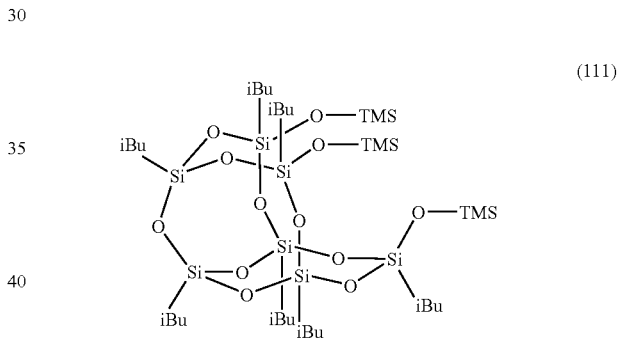

(111)

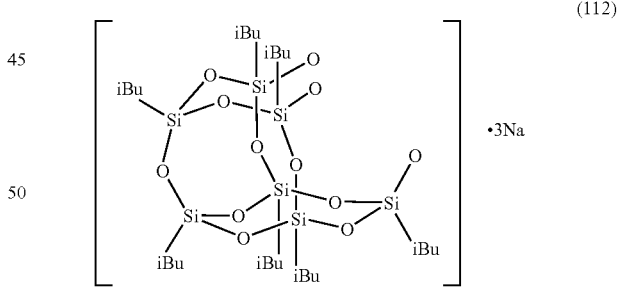

(112)

Example 13

Preparation of a Sodium-bound Isooctylsilsesquioxane Compound from Isooctyltrimethoxysilane A sodium-bound isooctylsilsesquioxane compound represented by formula (113) can be prepared as in example 3 except that in place of phenyltrimethoxysilane, isooctyltrimethoxysilane is used.

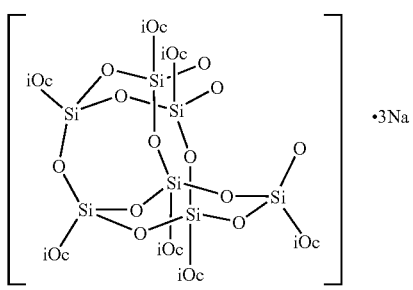

(113)

Example 14

Introduction of Trimethylsilyl Groups into a Compound (113)

An isooctylsilsesquioxane compound represented by formula (114) can be prepared as in example 4 except that in place of compound (104), a compound (113) is used. The product of said compound (113) can be verified by conducting structure analyses of the compound (114) as in example 4.

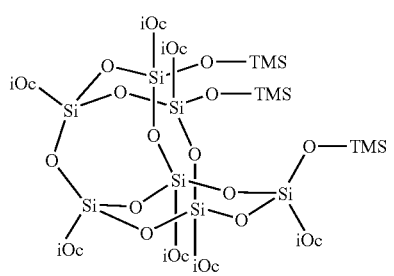

(114)

Example 15

Preparation of a Sodium-bound Trifluoropropylsilsesquioxane Compound from Trifluoropropyltrimethoxysilane Trifluoropropyltrimethoxysilane (100 g), tetrahydrofuran (500 mL), deionized water (10.5 g) and sodium hydroxide (7.9 g) were placed into a 1-L four-necked flask equipped with a reflux condenser, a thermometer, and a dropping funnel. The reactants were stirred with a magnetic stirrer and the flask was heated in an oil bath to the refluxing temperature of tetrahydrofuran. After five hours of reflux with stirring, the reaction was completed. The flask was removed from the oil bath and allowed to stand at room temperature overnight. The flask was placed in the oil bath again, and the content was concentrated by heating at a constant pressure until the solid was fully precipitated. The precipitate was filtered off using a 0.5-μm membrane fitted to a pressure filter. The resulting solid was washed once with tetrahydrofuran, and dried under reduced pressure and 80° C. for three hours to obtain a colorless powdery solid (74 g).

Example 16

Introduction of Trimethylsilyl Groups

The colorless powdery solid prepared in example 15 (1.0 g), tetrahydrofuran (10 g) and triethylamine (1.0 g) were placed into a 50-mL four-necked flask equipped with a dropping funnel, a reflux condenser, and a thermometer. The apparatus was purged with dry nitrogen and sealed. While the reactants were stirred with a magnetic stirrer, chlorotrimethylsilane (3.3 g) was added dropwise from the dropping funnel at room temperature over one minute. On completion of the addition, the content was stirred for another three hours to complete the reaction. Pure water (10 g) was added inside the flask to hydrolyze the resulting sodium chloride and unreacted chlorotrimethylsilane. The resulting mixture was transferred into a separating flask and the water layer was removed. The remaining organic layer was repeatedly washed with deionized water until the washing solution became neutral. The organic layer obtained was dehydrated with magnesium sulfate anhydride and the desiccant was removed by filtration. The filtrate was concentrated under reduced pressure with a rotary evaporator to obtain a white solid (0.9 g).

The structure of the white solid analyzed by gel permeation chromatography (GPC), $^1$H-NMR, $^{29}$Si-NMR, $^{13}$C-NMR, mass spectroscopy and X-ray. The GPC data indicated that the resulting white powdery solid was monodispersed, exhibited a weight-average molecular weight relative to polystyrene standards of 1570 and had a purity of 98 percent by weight. The $^1$H-NMR data revealed the integral ratio of trifluoropropyl groups to trimethylsilyl groups was 7:3. The $^{29}$Si-NMR data revealed three peaks that suggested a T-structure containing trifluoropropyl groups at an integral ratio of 1:3:3, and a peak that suggested a trimethylsilyl group at 12.11 ppm. The $^{13}$C-NMR data found peaks that suggested trifluoropropyl groups at 131 to 123 ppm, 28 to 27 ppm and 6 to 5 ppm, and a peak that suggested trimathylsilyl groups at 1.4 ppm. The mass spectrogram showed that the absolute molecular weight matched with the theoretical value of the structure with the formula (115). X-ray analysis indicated that the sample had the structure represented by formula (115). These analytical results indicate that the white powdery solid had the structure represented by formula (115) and suggests that the compound before trimethylsilanization had the structure represented by formula (116).

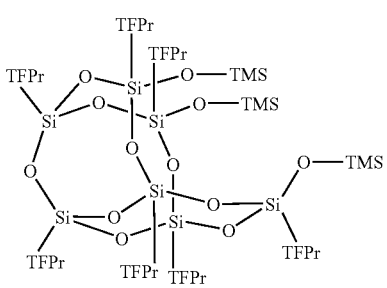

(115)

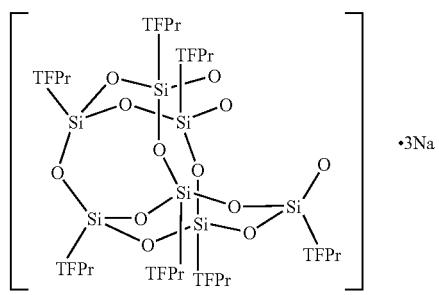

(116)

Example 17

Preparation of Acetoxyethyl-heptaphenyloctasilsesquioxane from a Compound (104)

The compound (104) prepared in example 1 (10 g) and tetrahydrofuran (200 mL) were placed into a 500-mL four-necked flask equipped with a stirrer bar, a reflux condenser and a thermometer. Acetoxyethyltrichlorosilane (3.3 g, 1.5 equivalent of the compound (104)) was rapidly added to the flask contents and the reactants were stirred at room temperature for two hours. The resulting liquid was then transferred into hexane (1000 g) and a solid was precipitated. The precipitate was filtered off under suction and dissolved in toluene (90 g). The organic layer was washed three times with water (330 mL) and dehydrated with magnesium sulfate anhydride (5 g). The desiccant was removed by filtration and the filtrate was concentrated to yield a solid precipitate. Ethanol (90 g) was added to the precipitate and the mixture was stirred at room temperature. The solid was filtered off under pressure and dried under reduced pressure (80° C., three hours) to obtain a colorless solid (6.88 g, yield: 65.9%).

Analysis by gel permeation chromatography of the resulting solid revealed only a singlet peak, suggesting the exclusion of impurities. The following IR, $^1$H-NMR, $^{13}$C-NMR and $^{29}$Si-NMR results show that the solid exhibits the structure represented by formula (117).

IR (KBr tablet method): ν=1740 (C=O), 1430 (Si-Ph), 1240 (C—O), 1135–1090 (Si-Ph), 1090–1000 (Si—O—Si) cm$^{-1}$ $^1$H NMR (400 MHz, TMS-standard: δ=0.0 ppm): 7.82–7.72, 7.46–7.31 (m, 35H, Ph-Si), 4.32–4.28 (t, 2H, —O—CH$_2$—), 1.84 (s, 3H, CH$_3$—(C=O)—), 1.37–1.33 (t, 2H, —CH$_2$—Si)

$^{13}$C NMR (100 MHz, TMS-standard: δ=0.0 ppm): 171.15 (C=O), 134.4–134.3, 131.1–131.0, 130.2, 128.12 (Ph-Si), 60.6 (—O—CH$_2$—), 20.8 (CH$_3$—(C=O)—), 13.2 (—CH$_2$—Si)

$^{29}$Si NMR (79 MHz, TMS-standard: δ=0.0 ppm): −67.97 (—CH$_2$—Si$_{1.5}$), −78.36, −78.67 (Ph-SiO$_{1.5}$)

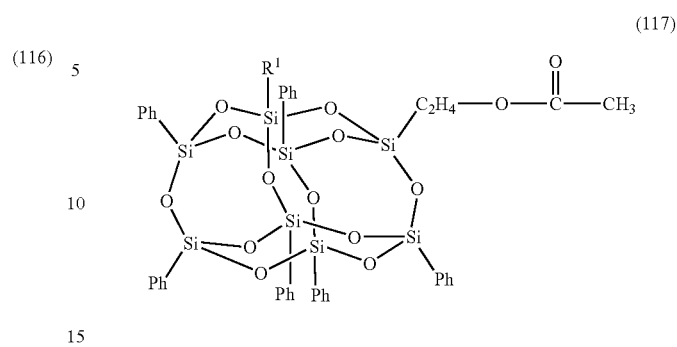

(117)

Example 18

Preparation of Acetoxyethyl-heptacyclohexyloctasilsesquioxane from a Compound (105)

A compound represented by formula (118) can be prepared as in example 17 except that in place of compound (104), the compound (105) prepared in example 5 is used.

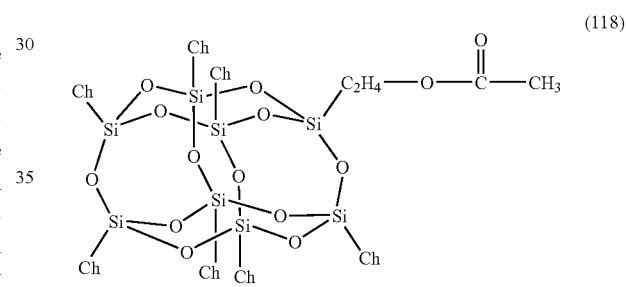

(118)

Example 19

Preparation of Acetocyethyl-heptacyclopentyloctasilsesquioxane from a Compound (108)

A compound represented by formula (119) can be prepared as in example 17 except that in place of compound (104), the compound (108) prepared in example 7 is used.

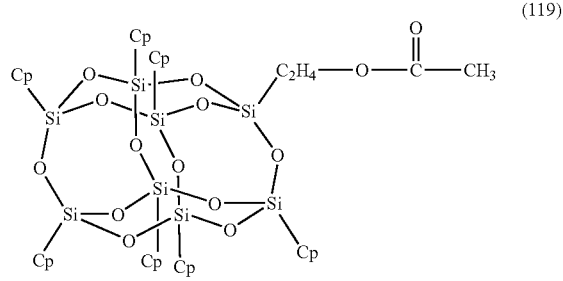

(119)

Example 20

Preparation of Acetoxyethyl-heptaethyloctasilsesquioxane from a Compound (109)

A compound represented by formula (120) can be prepared as in example 17 except that in place of compound (104), the compound (109) prepared in example 9 is used.

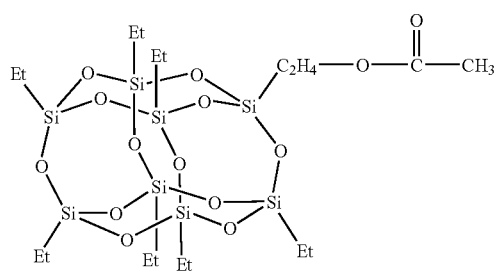

(120)

Example 21

Preparation of Acetoxyethyl-heptaisobutyloctasilsesquioxane from a Compound (112)

A compound represented by formula (121) can be prepared as in example 17 except that in place of compound (104), the compound (112) prepared in example 11 is used.

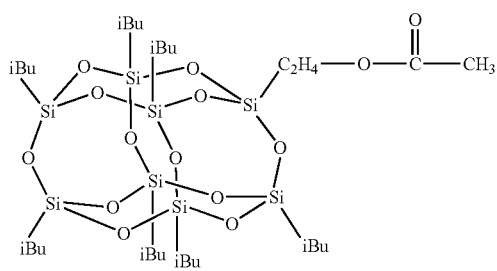

(121)

Example 22

Preparation of Acetoxyethyl-heptaisooctyloctasilsesquioxane from a Compound (113)

A compound represented by formula (122) can be prepared as in example 17 except that in place of compound (104), the compound (113) prepared in example 13 is used.

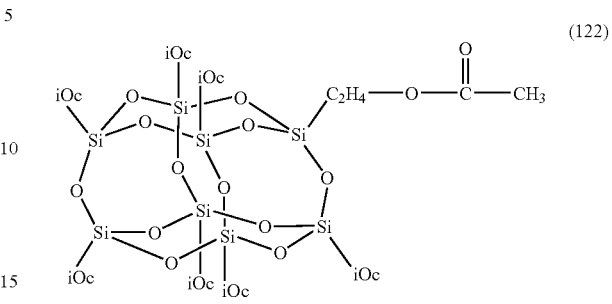

(122)

Example 23

Preparation of Acetoxyethyl-heptatrifluoropropyloctasilsesquioxane from a Compound (116)

The compound (116) prepared in example 15 (22.71 g) and tetrahydrofuran (400 g) were placed into a 500-mL four-necked flask equipped with a stirrer bar, a reflux condenser, a thermometer. Acetoxyethyltrichlorosilane (3.21 g, 1.6 equivalent of the compound (104)) was rapidly added to the flask contents and the reactants were stirred at room temperature for four hours. The reaction mixture was filtered off, and the filtrate was concentrated with a rotary evaporator. Methanol (100 mL) was added to the condensate, and the resulting solid was filtered off. Tetrahydrofuran (200 mL) was added to the solid and the solution was dehydrated with magnesium sulfate anhydride (5 g). The desiccant was removed by filtration and the filtrate was concentrated to yield a solid. Methanol (100 g) was added to the solid and stirred at room temperature. The solid was filtered off and dried under reduced pressure at 75° C. for five hours to obtain a colorless solid (12.2 g, yield: 51.6%).

Analysis of the solid by gel permeation chromatography revealed only a singlet peak, suggesting the exclusion of impurities. The following IR, $^1$H-NMR, $^{13}$C-NMR, and $^{29}$Si-NMR results show that the colorless solid exhibits the structure represented by formula (123).

$^1$H NMR (400 MHz, TMS-standard: δ=0.0 ppm): 4.18 (t, 2H, —O—CH$_2$—), 2.14 (m, 14H, —[CH$_2$]—CF$_3$), 2.04 (s, 3H, CH$_3$—(C=O)—), 1.19 (t, 2H, —CH$_2$—Si), 0.95 (m, 14H, Si—[CH$_2$]—CH$_2$—CF$_3$)

$^{13}$C NMR (100 MHz, TMS-standard: δ=0.0 ppm): 171.11 (C=O), 131.41, 128.68, 125.92, 123.20 (—CF$_3$), 60.01 (—O—CH$_2$—), 28.17, 27.85, 27.55, 27.25 (—[CH$_2$]—CF$_3$), 20.92 (CH$_3$—(C=O)—), 12.81 (—CH$_2$—Si), 4.03 (Si—[CH$_2$]—CH$_2$—CF$_3$)

$^{29}$Si NMR (79 MHz, TMS-standard: δ=0.0 ppm): −68.66 (—CH$_2$—SiO$_{1.5}$), −67.62, −67.72 (CF$_3$—CH$_2$—CH$_2$—SiO$_{1.5}$)

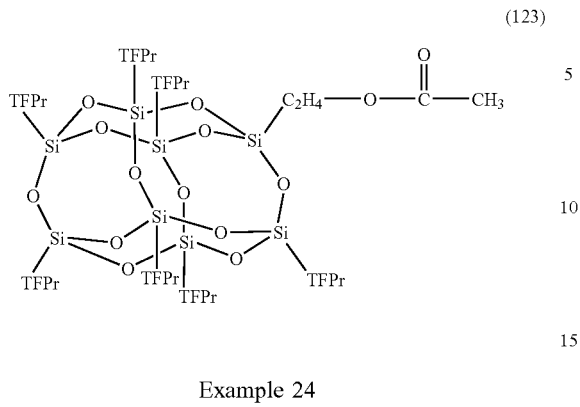

(123)

Example 24

Preparation of Acetoxyethyl-heptaphenyloctasilsesquioxane from a Compound (124)

A compound of formula (124) (10 g, trisilanolphenyl-POSS, Hybrid Plastics, U.S.), triethylamine (4.24 g, 1.3 equivalent of silanol), and tetrahydrofuran (200 mL) were placed into a 500-mL four-necked flask equipped with a stirrer bar, a dropping funnel, a reflux condenser, and a thermometer and immersed in an ice bath. Acetoxyethyl-trichlorosilane (3.32 g, 1.5 equivalent of the compound (124)) was rapidly added to the flask contents and the reactants were stirred at room temperature for two hours. The resulting liquid was transferred into hexane (1000 g), and a solid was formed. The solid was filtered off under suction and then dissolved in toluene (90 g). The organic layer was washed three times with water (330 mL) and dehydrated with magnesium sulfate anhydride (5 g). The desiccant was removed by filtration. Ethanol (90 g) was added to the solid obtained through concentration of the filtrate, and the mixture was stirred at room temperature. The remaining solid was filtered off and dried under vacuum at 80° C. for three hours to obtain a colorless solid (5.25 g, yield: 47.0%).

Analysis by gel permeation chromatography of the colorless solid revealed only a singlet peak, suggesting the exclusion of impurities. The following IR, $^1$H-NMR, $^{13}$C-NMR and $^{29}$Si-NMR results show that the colorless solid exhibits the structure represented by formula (117).

IR (KBr tablet method): ν=1740 (C=O), 1430 (Si-Ph), 1240 (C—O), 1135–1090 (Si-Ph), 1090–1000 (Si—O—Si) cm$^{-1}$ $^1$H NMR (400 MHz, TMS-standard: δ=0.0 ppm): 7.82–7.72, 7.46–7.31 (m, 35H, Ph-Si), 4.32–4.28 (t, 2H, —O—CH$_2$—), 1.84 (s, 3H, CH$_3$—(C=O)—), 1.37–1.33 (t, 2H, —CH$_2$—Si)

$^{13}$C NMR (100 MHz, TMS-standard: δ=0.0 ppm): 171.15 (C=O), 134.4–134.3, 131.1–131.0, 130.2, 128.12 (Ph-Si), 60.6 (—O—CH$_2$—), 20.8 (CH$_3$—(C=O)—), 13.2 (—CH$_2$—Si)

$^{29}$Si NMR (79 MHz, TMS-standard: δ=0.0 ppm): −67.97 (—CH$_2$—SiO$_{1.5}$), −78.36, −78.67 (Ph-SiO—$_{1.5}$)

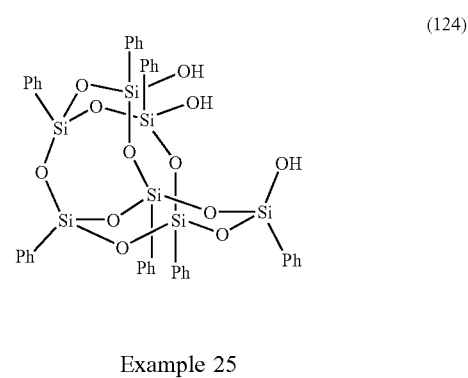

(124)

Example 25

Preparation of Acetoxyethyl-heptacyclohexyloctasilsesquioxane from a Compound (125)

The compound (118) described in example 18 can be prepared as in example 24 except that in place of compound (124), a compound represented by formula (125) (trisilanol-cyclohexyl-POSS, Hybrid Plastics, U.S.) is used.

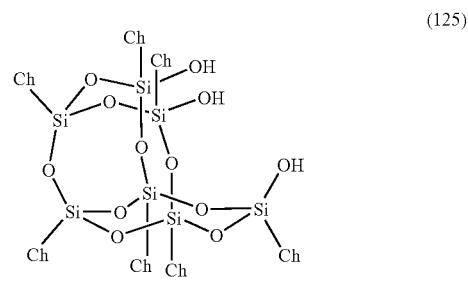

(125)

Example 26

Preparation of Acetoxyethyl-heptacyclopentyloctasilsesquioxane form a Compound (126)

The compound (119) described in example 19 can be prepared as in example 24 except that in place of compound (124), a compound represented by formula (126) (trisilanol-cyclopentyl-POSS, Hybrid Plastics, U.S.) is used.

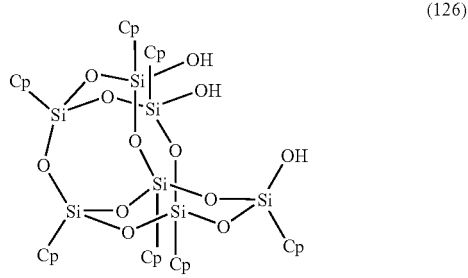

(126)

Example 27

Preparation of Acetoxyethyl-heptaethyloctasilsesquioxane from a Compound (127)

The compound (120) described in example 20 can be prepared as in example 24 except that in place of compound (124), a compound represented by formula (127) (trisilano-lethyl-POSS, Hybrid Plastics, U.S.) is used.

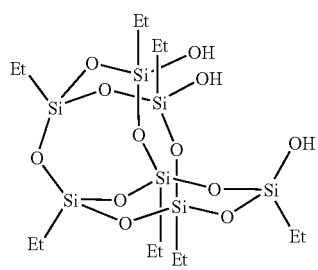

(127)

Example 28

Preparation of Acetoxyethyl-heptaisobutyloctasilsesquioxane from a Compound (128)

The compound (121) described in example 21 can be prepared as in example 24 except that in place of compound (124), a compound represented by formula (128) (trisilano-lisobutyl-POSS, Hybrid Plastics, U.S.) is used.

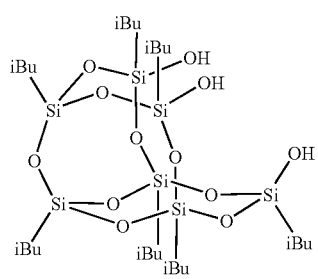

(128)

Example 29

Preparation of Acetoxyethyl-heptaisooctyloctasilsesquioxane from a Compound (129)

The compound (122) described in example 22 can be prepared as in example 24 except that in place of compound (124), a compound represented by formula (129) (trisilano-lisooctyl-POSS, Hybrid Plastics, U.S.) is used.

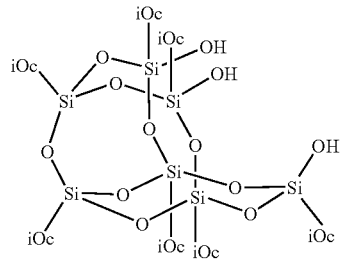

(129)

Example 30

Preparation of a Silanol-containing Heptatrifluoropropylsilsesquioxane Compound from a Compound (116)

The compound (116) prepared in example 15 (5 g) was placed into a 300-mL four-necked flask equipped with a stirrer bar, a dropping funnel, a reflux condenser, and a thermometer and immersed in an ice bath. Butyl acetate (50 g) was added to the flask contents to dissolve the compound. Acetic acid (0.5 g) was added dropwise, and the reactants were stirred in the ice bath for one hour. The flask was removed from the bath, and allowed to stand to room temperature. The resulting liquid was washed three times with deionized water (100 mL). The solvent was removed with a rotary evaporator and the resulting product was dried under reduced pressure at 50° C. for one hour to obtain a glutinous liquid (4.3 g).

Analysis of the resulting compound by gel permeation chromatography revealed only a singlet peak, suggesting the exclusion of impurities. An IR analysis of the compound revealed existence of an absorption band (at and around 3400 cm$^{-1}$) that suggests the presence of silanol groups which were not observed in the IR data of compound (116). These results suggest that the resulting compound exhibits the structure represented by formula (130).

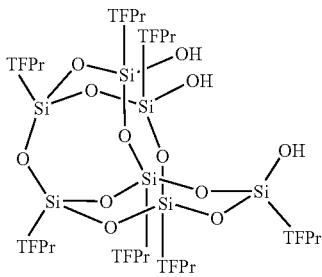

(130)

Preparation of Acetoxyethyl-heptatrifluoropropyloctasilsesquioxane from a Compound (130)

A compound (123) can be prepared by reacting acetoxyethyltrichlorosilane with compound (130) in the presence of triethylamine as in examples 24 to 29.

Example 31

Preparation of a Raw Material of Acetoxypropyl-heptaphenyloctasilsesquioxane from a Compound (104)

The compound (104) prepared in example (10 g), triethylamine (1.5 g) and tetrahydrofuran (200 mL) were placed into a 500-mL four-necked flask equipped with a stirrer bar, a reflux condenser and a thermometer. Acetoxypropyl-trichlorosilane (3.5 g, 1.5 equivalent of the compound (104)) was added to the flask contents and the reactants were stirred at room temperature for two hours. The resulting liquid was added into hexane (1000 g) and a solid was precipitated. The precipitate was filtered off under suction and dissolved in toluene (90 g). The organic layer was washed three times with water (330 mL) and dehydrated with magnesium sulfate anhydride (5 g). The desiccant was removed by filtration. The filtrate was concentrated to obtain a solid. Ethanol (90 g) was added to the solid and the mixture was stirred at room temperature. The solid was filtered off under pressure and dried under reduced pressure at 80° C. for three hours to obtain a colorless solid (7.15 g, yield: 67.6%).

Analysis of the resulting product by gel permeation chromatography revealed only a singlet peak, suggesting the exclusion of impurities. The following IR, $^1$H-NMR, $^{13}$C-NMR, and $^{29}$Si-NMR results show that the solid exhibits the structure represented by formula (131).

IR (KBr tablet method): ν=1740 (C=O), 1430 (Si-Ph), 1240 (C—O), 1135–1090 (Si-Ph), 1090–1000 (Si—O—Si) cm$^{-1}$ $^1$H NMR (400 MHz, TMS-standard: δ=0.0 ppm): 7.82–7.72, 7.46–7.31 (m, 35H, [Ph]-Si), 4.07–4.04 (t, 2H, —O—[CH$_2$]—), 1.94 (s, 3H, [CH$_3$]—(C=O)—), 1.84–1.88 (tt, 2H, —CH$_2$—[CH$_2$]—CH$_2$—), 1.37–1.33 (t, 2H, —[CH$_2$]—Si)

$^{13}$C NMR (100 MHz, TMS-standard: δ=0.0 ppm): 171.10 (C=O), 134.4–134.3, 131.1–131.0, 130.2, 128.12 (Ph-Si), 66.2 (—O—CH$_2$—), 22.2 (—CH$_2$—[CH$_2$]—CH$_2$—), 20.9 ([CH$_3$]—(C=O)—), 8.26 (—[CH$_2$]—Si)

$^{29}$Si NMR (79 MHz, TMS-standard: δ=0.0 ppm): −65.30 (—CH$_2$—SiO$_{1.5}$), −78.26, −78.62 (Ph-SiO$_{1.5}$)

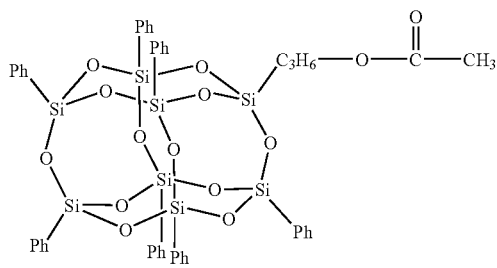

(131)

Example 32

Preparation of Acetoxypropyl-heptacyclohexyloctasilsesquioxane from a Compound (105)

A compound represented by formula (132) can be prepared as in example 31 except that in place of compound (104), the compound (105) prepared in example 5 is used.

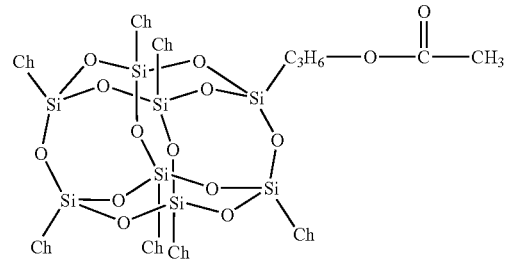

(132)

Example 33

Preparation of Acetoxypropyl-heptacyclopentyloctasilsesquioxane from a Compound (108)

A compound represented by formula (133) can be prepared as in example 31 except that in place of compound (104), the compound (108) prepared in example 7 is used.

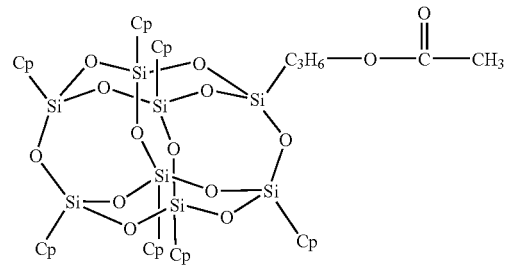

(133)

Example 34

Preparation of Acetoxypropyl-heptaethyloctasilsesquioxane from a Compound (109)

A compound represented by formula (134) can be prepared as in example 31 except that in place of compound (104), the compound (109) prepared in example 9 is used.

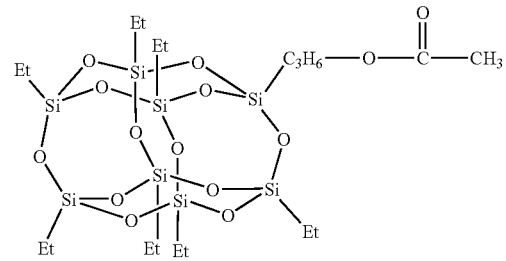

(134)

Example 35

Preparation of Acetoxypropyl-heptaisobutyloctasilsesquioxane from a Compound (112)

A compound represented by formula (135) can be prepared as in example 31 except that in place of compound (104), the compound (112) prepared in example 11 is used.

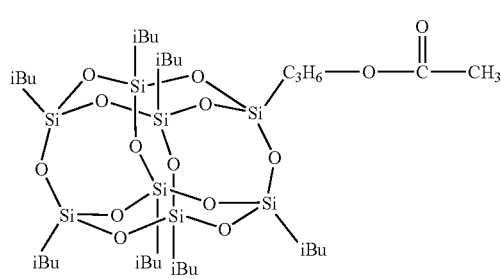
(135)

Example 36

Preparation of Acetoxypropyl-heptaisooctyloctasilsesquioxane from a Compound (113)

A compound represented by formula (136) can be prepared as in example 31 except that in place of compound (104), the compound (113) prepared in example 13 is used.

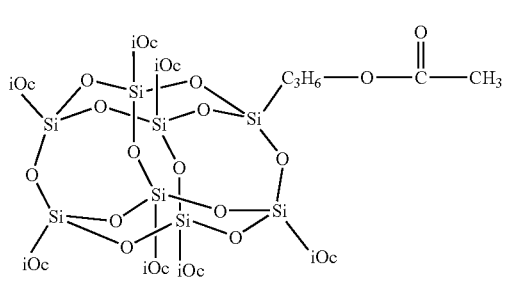
(136)

Example 37

Preparation of Acetoxypropyl-heptatrifluoropropyloctasilsesquioxane form a Compound (116)

A compound represented by formula (137) can be prepared according to the reaction conditions described in example 31 and purification conditions described in example 23 except that in place of compound (104), the compound (116) prepared in example 15 is used.

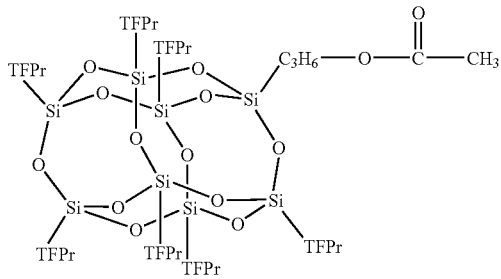
(137)

Example 38

Preparation of Acetoxypropyl-heptaphenyloctasilsesquioxane from a Compound (124)

The compound (131) described in example 31 can be prepared by reacting a compound represented by formula (124) (trisilanolphenyl-POSS, Hybrid Plastics, U.S.) described in example 24 with acetoxypropyltrichlorosilane (1.5 equivalent of a compound (124)) in tetrahydrofuran in the presence of triethylamine (1.3 equivalent of silanol).

Example 39

Preparation of Acetoxypropyl-heptacyclohexyloctasilsesquioxane from a Compound (125)

A compound (132) described in example 32 can be prepared as in example 38 except that in place of compound (124), a compound represented by formula (125) (trisilanol-cyclohexyl-POSS, Hybrid Plastics, U.S.) is used.

Example 40

Preparation of Acetoxypropyl-heptacyclopentyloctasilsesquioxane from a Compound (126)

The compound (133) described in example 33 can be prepared as in example 38 except that in place of compound (124), a compound represented by formula (126) (trisilanol-cyclopentyl-POSS, Hybrid Plastics, U.S.) is used.

Example 41

Preparation of Acetoxypropyl-heptaethyloctasilsesquioxane from a Compound (127)

The compound (134) described in example 34 can be prepared as in example 38 except that in place of compound (124), a compound represented by formula (127) (trisilanolethyl-POSS, Hybrid Plastics, U.S.) is used.

Example 42

Preparation of Acetoxypropyl-heptaisobutyloctasilsesquioxane from a Compound (128)

The compound (135) described in example 35 can be prepared as in example 38 except that in place of compound (124), a compound represented by formula (128) (trisilanolisobutyl-POSS, Hybrid Plastics, U.S.) is used.

Example 43

Preparation of Acetoxypropyl-heptaisooctyloctasilsesquioxane from a Compound (129)

The compound (136) described in example 36 can be prepared as in example 38 except that in place of compound (124), a compound represented by formula (129) (trisilanolisooctyl-POSS, Hybrid Plastics, U.S.) is used.

Example 44

Preparation of Acetoxypropyl-heptatrifluoropropyloctasilsesquioxane form a Compound (130)

The compound (137) described in example 37 can be prepared by reacting acetoxyethyltrichlorosilane in the presence of triethylamine as in examples 31 to 43 except that in place of compound (124), a compound represented by formula (130) is used.

Example 45

Preparation of Hydroxyethyl-heptaphenyloctasilsesquioxane from a Compound (117)

The compound (117) prepared in example 17 (2.58 g) was placed into a 500-mL round-bottom flask containing a stirring bar. A mixed solution (300 mL) of methanol (174.7 mL), chloroform (174.3 mL) and sulfuric acid (36N, 0.7 mL) were added into the flask, and the reactants were stirred at room temperature for 72 hours. The resulting solution was concentrated with a rotary evaporator, and the concentrate was dissolved in ethyl acetate (500 mL). The organic layer was washed with water (500 mL) in a separating funnel, and dehydrated with magnesium sulfate anhydride (5 g). The desiccant was removed by filtration and the filtrate was concentrated with a rotary evaporator. The concentrate was dried and a colorless solid (2.37 g, yield: 91.7%) was obtained. The solid (1.09 g) was recrystallized in toluene. The solvent was removed under reduced pressure to obtain a colorless solid (0.48 g, yield: 43.7%).

Analysis of the resulting product by gel permeation chromatography revealed only a singlet peak, indicating the exclusion of impurities. The following IR, $^1$H-NMR, $^{13}$C-NMR, and $^{29}$Si-NMR results show that the product exhibits the structure represented by formula (138).

IR (KBr tablet method): ν=3600–3200 (OH), 1420 (Si-Ph), 1135–1090 (Si-Ph), 1090–1000 (Si—O—Si) cm$^{-1}$ $^1$H NMR (400 MHz, TMS-standard: δ=0.0 ppm): 7.82–7.72, 7.46–7.31 (m, 35H, Ph-Si), 3.85–3.87 (t, 2H, —CH$_2$—O—), 1.42–1.62 (broad, 1H, —OH), 1.26–1.31 (t, 2H, Si—CH$_2$—)

$^{13}$C NMR (100 MHz, TMS-standard: δ=0.0 ppm): 134.5–134.1, 131.1–131.0, 130.3, 128.11–127.9 (Ph-Si), 58.6 (—CH$_2$—OH), 17.5 (Si—CH$_2$—)

$^{29}$Si NMR (79 MHz, TMS-standard: δ=0.0 ppm): −67.31 (—CH$_2$—SiO$_{1.5}$), −78.42, −78.79 (Ph-SiO$_{1.5}$)

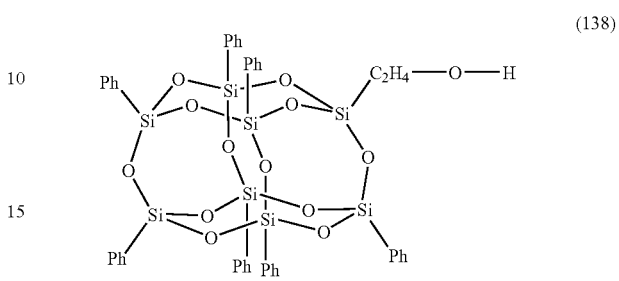

(138)

The compound (138) prepared in example 24 can be derived from compound (117) according to the above procedures.

Example 46

Preparation of Hydroxyethyl-heptaphenyloctasilsesquioxane from a Compound (117)

A colorless solid (0.09 g, yield: 94.7%) was obtained through reaction conducted as in example 2 except that the reactants were replaced by compound (117) prepared in example 17 (0.1 g), methanol (66.6 mL), chloroform (100 mL), and sulfuric acid (36N, 0.3 mL). A colorless solid (0.09 g, yield: 94.7%) was obtained. The following IR, $^1$H-NMR, $^{13}$C-NMR, and $^{29}$Si-NMR results show that the resulting product exhibits the structure represented by formula (138).

IR (KBr tablet method): ν=3600–3200 (OH), 1420 (Si-Ph), 1135–1090 (Si-Ph), 1090–1000 (Si—O—Si) cm$^{-1}$ $^1$H NMR (400 MHz, TMS-standard: δ=0.0 ppm): 7.82–7.72, 7.46–7.31 (m, 35H, Ph-Si), 3.85–3.87 (t, 2H, —CH$_2$—O—), 1.42–1.62 (broad, 1H, —OH), 1.26–1.31 (t, 2H, Si—CH$_2$—)

$^{13}$C NMR (100 MHz, TMS-standard: δ=0.0 ppm): 134.5–134.1, 131.1–131.0, 130.3, 128.11–127.9 (Ph-Si), 58.6 (—CH$_2$—OH), 17.5 (Si—CH$_2$—)

$^{29}$Si NMR (79 MHz, TMS-standard: δ=0.0 ppm): −67.31 (—CH$_2$—SiO$_{1.5}$), −78.42, −78.79 (Ph-SiO$_{1.5}$)

The compound (138) prepared in example 24 can be derived from a compound (117) according to the above procedures.

Example 47

Transesterification of a Compound (117) in Chloroform/methanol/sulfuric Acid A colorless solid (0.064 g, yield: 67.4%) was obtained through a reaction conducted as in example 2 except that the reactants were replaced by compound (117) prepared in example 17 (0.1 g), ethanol (83.3 mL), chloroform (83.3 mL), and sulfuric acid (36 N, 0.3 mL). IR analysis of the resulting product revealed the existence of an absorption band that suggested an acetoxy group at 1740 cm$^{-1}$. $^1$H-NMR analysis revealed that the product consists of a compound (138) and the compound (117) (content of compound (138): 66.3 mol %).

Example 48

Transesterification of a Compound (117) in Chloroform/methanol/sulfuric Acid

A colorless solid (0.078 g, yield: 82.1%) was obtained through a reaction conducted as in example 2 except that the reactants were replaced by the compound (117) prepared in example 17 (0.1 g), ethanol (66.6 mL), chloroform (100 mL), and sulfuric acid (36 N, 0.3 mL), and the reaction time was adjusted to 96 hours. IR analysis of the product revealed the existence of an absorption band that suggested an acetoxy group at 1740 cm$^{-1}$. $^1$H-NMR analysis revealed the product consists of a compound (138) and the compound (117) (content of compound (138): 90.1 mol %).

Example 49

Preparation of Hydroxyethyl-heptacyclohexyloctasilsesquioxane from a Compound (118)

A compound represented by formula (139) can be prepared as in example 45 except that in place of compound (117), the compound (118) prepared in example 18 or 25 is used.

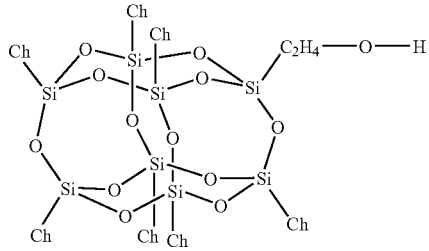

(139)

Example 50

Preparation of Hydroxyethyl-heptacyclopentyloctasilsesquioxane from a Compound (119)

A compound represented by formula (140) can be prepared as in example 45 except that in place of compound (117), the compound (119) prepared in example 19 or 26 is used.

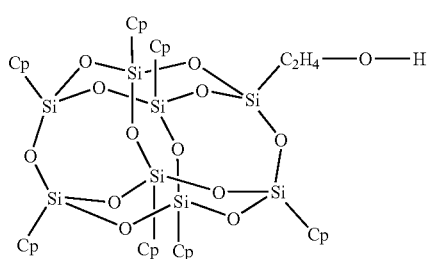

(140)

Example 51

Preparation of Hydroxyethyl-heptaethyloctasilsesquioxane from a Compound (120)

A compound represented by formula (141) can be prepared as in example 45 except that in place of compound (117), the compound (120) prepared in example 20 or 27 is used.

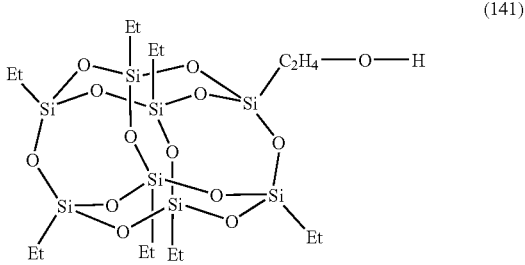

(141)

Example 52

Preparation of Hydroxyethyl-heptaisobutyloctasilsesquioxane from a Compound (121)

A compound represented by formula (142) can be prepared as in example 45 except that in place of compound (117), the compound (121) prepared in example 21 or 28 is used.

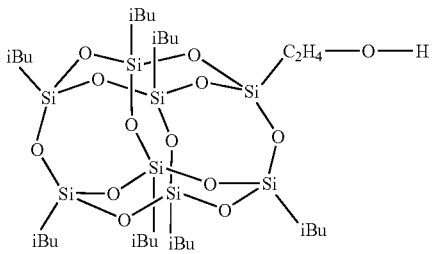

(142)

Example 53

Preparation of Hydroxyethyl-heptaisooctyloctasilsesquioxane from a Compound (122)

A compound represented by formula (143) can be prepared as in example 45 except that in place of compound (117), the compound (122) prepared in example 22 or 29 is used.

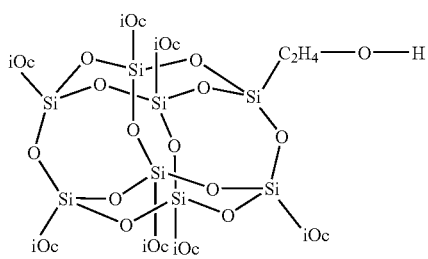

(143)

Example 54

Preparation of Hydroxyethyl-heptatrifluoropropyloctasilsesquioxane from a Compound (123)

The compound (123) prepared in example 23 (3.5 g) was placed into a 1-L three-necked flask equipped with a stirrer bar, a reflux condenser, and a thermometer. A mixture of methanol (359.5 mL), AK-225 (HCFC-225: $CF_3CF_2CHCl_2$/$CClF_2CF_2CHClF$, Asahi Glass Co., 239.6 mL), and sulfuric acid (36 N, 0.9 mL) was added to the flask contents and the reactants were stirred at room temperature for 12 hours. The flask was heated to 45° C. and the stirring was continued at that temperature for another 9 hours. The resulting solution was concentrated with a rotary evaporator, and the concentrate was dissolved in AK-225 (200 mL). The organic layer was washed with water (500 mL) in a separating flask, and dehydrated with magnesium sulfate anhydride (5 g). The desiccant was removed by filtration, the filtrate was condensed with a rotary evaporator, and the condensate was dried to obtain a colorless solid (3.04 g, yield: 89.9%).

Analysis of the resulting product by gel permeation chromatography revealed only a singlet peak, indicating the exclusion of impurities. The following $^1$H-NMR, $^{13}$C-NMR and $^{29}$Si-NMR results show that the product exhibits the structure represented by formula (144).

$^1$H NMR (400 MHz, TMS-standard: δ=0.0 ppm): 3.81 (t, 2H, —$CH_2$—O—), 2.14 (m, 14H, —[$CH_2$]—$CF_3$), 1.39 (broad, 1H, —OH), 1.13 (t, 2H, Si—[$CH_2$]—$CH_2$—OH), 0.93 (m, 14H, Si—[$CH_2$]—$CH_2$—$CF_3$)

$^{13}$C NMR (100 MHz, TMS-standard: δ=0.0 ppm): 131.31, 128.58, 125.83, 123.11 (—$CF_3$), 58.08 (—$CH_2$—OH), 28.12, 27.83, 27.52, 27.22 (—[$CH_2$]—$CF_3$), 19.74 (—$CH_2$—Si), 4.02 (Si—[$CH_2$]—$CH_2$—$CF_3$)

$^{29}$Si NMR (79 MHz, TMS-standard: δ=0.0 ppm): −67.84 (—$CH_2$—$SiO_{1.5}$), −67.65, −67.66, −67.84 ($CF_3$—$CH_2$—$CH_2$—$SiO_{1.5}$)

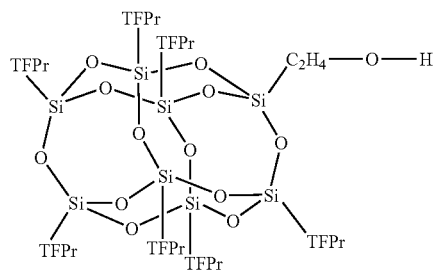

(144)

A compound (144) can be derived from the compound (123) prepared in example 30 according to the above procedures.

Example 55

Transesterification of a Compound (123) in Chloroform/methanol/sulfuric Acid A colorless solid (yield: 93.1%) was obtained through reaction conducted as in example 54 except that the reactants were replaced by the compound (123) prepared in example 23 (0.5 g), methanol (42.7 mL), AK-225 (42.7 mL), and sulfuric acid (36 N, 0.26 mL). $^1$H-NMR analysis revealed that the product consists of a compound (144) and the compound (123) (content of compound (144): 89.4 mol %).

Example 56

Transesterification of a Compound (123) in Chloroform/methanol/sulfuric Acid A white solid (yield: 92.2%) was obtained through reaction conducted as in example 54 except that the reactants were replaced by the compound (123) prepared in example 23 (0.5 g), methanol (42.7 mL), AK-225 (42.7 mL) and sulfuric acid (36 N, 0.26 mL), the reaction temperature was lowered to room temperature, and the reaction time was extended to 72 hours. $^1$H-NMR data showed that the product consisted of a compound (144) and the compound (123) (content of compound (144): 91.3 mol %).

Example 57

Transesterification of a Compound (123) in Chloroform/methanol/sulfuric Acid A colorless solid (yield: 91.0%) was obtained through reaction conducted as in example 54 except that the reactants were replaced by the compound (123) prepared in example 23 (0.5 g), methanol (42.7 mL), chloroform (42.7 mL) and sulfuric acid (36 N, 0.26 mL), the reaction temperature was lowered to room temperature, and the reaction time was extended to 72 hours. $^1$H-NMR data showed that the product consisted of a compound (144) and the compound (123) (content of compound (144): 81.5 mol %).

Example 58

Transesterification of a Compound (123) in Chloroform/methanol/sulfuric Acid A colorless solid (yield: 90.9%) was obtained through reaction conducted as in example 54 except that the reactants were replaced by the compound (123) prepared in example 23 (0.5 g), methanol (42.7 mL), chloroform (42.7 mL) and p-toluene sulfonate (4.43 g), the reaction temperature was lowered to room temperature and the reaction time was extended to 72 hours. $^1$H-NMR data showed that the product consisted of a compound (144) and the compound (123) (content of compound (144): 89.0 mol %).

Example 59

Preparation of Hydroxypropyl-heptaphenyloctasilsesquioxane from a Compound (131)

The compound (131) prepared in example 31 (2.5 g), and a mixed solution (417.4 mL) of methanol (208.3 mL), chloroform (208.3 mL) and sulfuric acid (36 N, 0.75 mL) were placed into a 500-mL round-bottom flask containing a stirring bar. The reactants were stirred at room temperature for 72 hours. The resulting liquid was concentrated with a rotary evaporator. The condensate was dissolved in ethyl acetate (500 mL). The organic layer was washed with water (500 mL) in a separating funnel and dehydrated with magnesium sulfate anhydride (5.0 g). After the desiccant was removed by filtration, the filtrate was concentrated with a rotary evaporator to yield a solid. The solid was dried to obtain a colorless solid (2.35 g, yield: 97.9%). The solid was washed with ethanol and the washing solution removed through suction filtration to obtain a colorless solid (compound G) (1.26 g, yield: 52.5%).

Analysis of the resulting product by gel permeation chromatography revealed only a singlet peak, indicating the exclusion of impurities. The following IR, $^1$H-NMR, $^{13}$C-NMR and $^{29}$Si-NMR results show that the product exhibits the structure represented by formula (145).

IR (KBr tablet method): ν=3600–3200 (OH), 1420 (Si-Ph), 1135–1090 (Si-Ph), 1090–1000 (Si—O—Si) cm$^{-1}$ $^1$H NMR (400 MHz, TMS-standard: δ=0.0 ppm): 7.82–7.72, 7.48–7.32 (m, 35H, [Ph]-Si), 3.62–3.57 (t, 2H, —[CH$_2$]—O—), 1.2 (broad, 1H, —[OH], 1.78–1.74 (tt, 2H, —CH$_2$—[CH$_2$]—CH$_2$—), 0.90–0.86 (t, 2H, Si—[CH$_2$]—)

$^{13}$C NMR (100 MHz, TMS-standard: δ=0.0 ppm): 134.5–134.4, 131.1–131.0, 130.6–130.4, 128.2–128.1 ([Ph]-Si), 65.0 (—[CH$_2$]—OH), 26.1 (—CH$_2$—[CH$_2$]—CH$_2$—), 7.9 (Si—[CH$_2$]—)

$^{29}$Si NMR (79 MHz, TMS-standard: δ=0.0 ppm): –65.08 (—CH$_2$—SiO$_{1.5}$), –78.55, –78.94 (Ph-SiO$_{1.5}$)

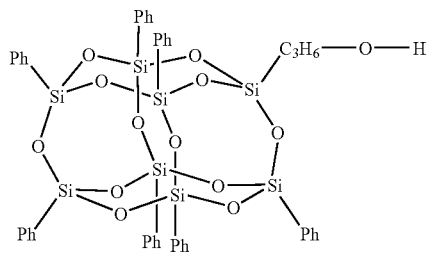

(145)

A compound (145) can be derived from the compound (131) prepared in example 38 according to the above procedures.

Example 60

Preparation of Hydroxypropyl-heptacyclohexyloctasilsesquioxane from a Compound (132)

A compound represented by formula (146) can be prepared as in example 59 except that in place of compound (131), the compound (132) prepared in example 32 or 39 is used.

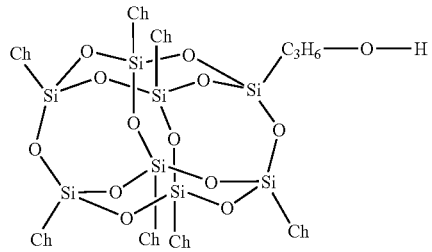

(146)

Example 61

Preparation of Hydroxypropyl-heptacyclopentyloctasilsesquioxane from a Compound (133)

A compound represented by formula (147) can be prepared as in example 59 except that in place of compound (131), the compound (133) prepared in example 33 or 40 is used.

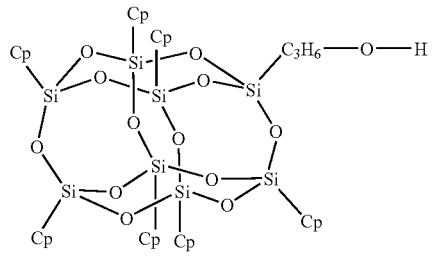

(147)

Example 62

Preparation of Hydroxypropyl-heptaethyloctasilsesquioxane from a Compound (134)

A compound represented by formula (148) can be prepared as in example 45 except that in place of compound (131), the compound (134) prepared in example 34 or 41 is used.

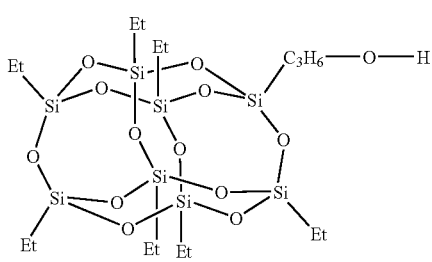

(148)

Example 63

Preparation of Hydroxypropyl-heptaisobutyloctasilsesquioxane from a Compound (135)

A compound represented by formula (149) can be obtained as in example 45 except that in place of compound (131), the compound (135) prepared in example 35 or 42 is used.

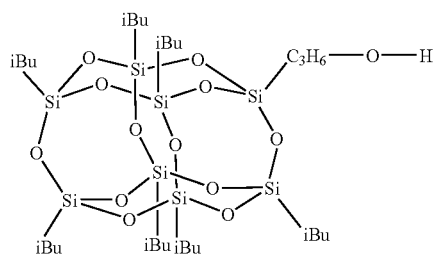
(149)

Example 64

Preparation of Hydroxypropyl-heptaisooctyloctasilsesquioxane from a Compound (136)

A compound represented by formula (150) can be prepared as in example 45 except that in place of compound (131), the compound (136) prepared in example 36 or 43 is used.

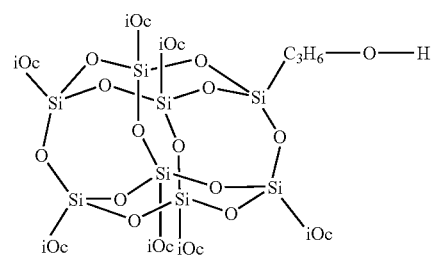
(150)

Example 65

Preparation of Hydroxypropyl-heptatrifluoropropyloctasilsesquioxane from a Compound (137)

A compound represented by formula (151) can be prepared as in example 54 except that in place of compound (131), the compound (137) prepared in example 37 or 44 is used.

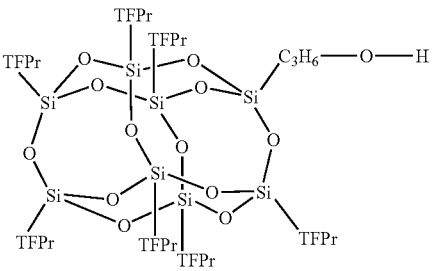
(151)

Example 66

Preparation of a compound of sodium-bound tridecafluoro-1,1,2,2-tetrahydrooctylsilsesquioxane from tridecafluoro-1,1,2,2-tetrahydrooctyltriethoxysilane Tridecafluoro-1,1,2,2-tetrahydrooctyltriethoxysilane (4.9 g), tetrahydrofuran (15 mL), sodium hydroxide (0.2 g), and ion-exchange water (0.2 g) were placed into a 50-mL four-necked flask equipped with a stirring bar, a reflux condenser, a thermometer and a dropping funnel. The reactants were stirred at the reflux temperature of 75° C. After five hours of reflux with stirring, the reaction was completed. The resulting solution was condensed by heating under reduced pressure. The condensate was dried with a vacuum dryer at 80° C. for three hours to obtain a glutinous liquid (4.0 g).

Example 67

Introduction of Trimethylsilyl Groups

The above powdery solid (2.6 g), tetrahydrofuran (10 g), triethylamine (1.0 g) and trimethylchlorosilane (3.3 g) were placed into a 50-mL three necked flask, and stirred with a magnetic stirrer at room temperature for three hours. After the reaction was completed, treatment procedures were applied as in example 16 to obtain a glutinous liquid (1.3 g).

Analysis by gel permeation chromatography showed that the resulting product was monodispersed, possessed a weight-average molecular weight relative to polystyrene standards of 3650 (uncorrected) and had a purity of 100%. These results, combined with those of examples 3 to 16, suggest the resulting liquid was the silicon compound of formula (152). This suggests that the compound prepared in example 66 exhibited the structure represented by formula (153).

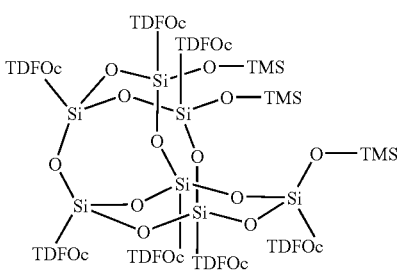
(152)

-continued

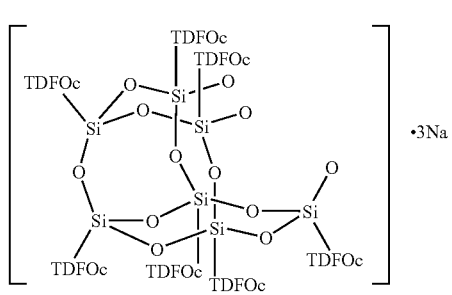

(153)

·3Na

Example 68

Preparation of a compound of silanol-containing tridecafluoro-1,1,2,2-trahydrooctylsilsesquioxane from a compound (153)

A compound represented by formula (154) can be prepared as in example 30 except that the starting material is a compound (153), and in place of butyl acetate, AK225 is used as the reaction solvent.

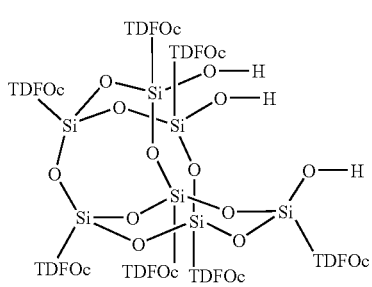

(154)

Example 69

Preparation of acetoxyethyl-heptatridecafluoro-1,1,2,2-tetrahydrooctyloctasilsesquioxane from a compound (153)

A compound represented by formula (155) can be prepared as in example 23 except that the starting material is a compound (153), and in place of tetrahydrofuran, AK225 is used as the reaction solvent.

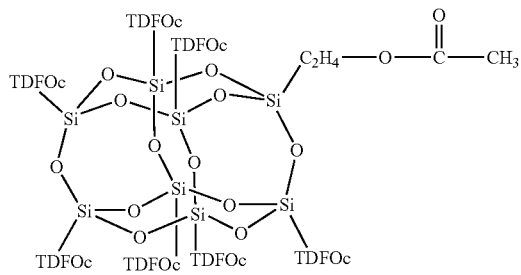

(155)

Example 70

Preparation of acetoxypropyl-heptatridecafluoro-1,1,2,2-tetrahydrooctyloctasilsesquioxane from a compound (153)

A compound represented by formula (156) can be prepared as in example 31 except that the starting material is a compound (153), and in place of tetrahydrofuran, AK225 is used as the reaction solvent.

(156)

Example 71

Preparation of acetoxyethyl-heptatridecafluoro-1,1,2,2-tetrahydrooctyloctasilsesquioxane from a compound (154)

A compound (155) can be prepared by reacting a compound (154) with acetoxyethyltrichlorosilane in the presence of triethylamine as in examples 24 to 30 except that the starting material is a compound (154) and the reaction solvent is AK225.

Example 72

Preparation of acetoxypropyl-heptatridecafluoro-1,1,2,2-tetrahydrooctyloctasilsesquioxane from a compound (154)

A compound (156) can be prepared by reacting acetoxyethyltrichlorosilane in the presence of triethylamine as in examples 38 to 44 except that the starting material is a compound (154) and the reaction solvent is AK225.

Example 73

Preparation of hydroxyethyl-heptatridecafluoro-1,1,2,2-tetrahydrooctyloctasilsesquioxane from a compound (155)

A compound represented by formula (157) can be prepared as in examples 54 to 58 except that the starting material is the compound (155) prepared in example 69 or 71.

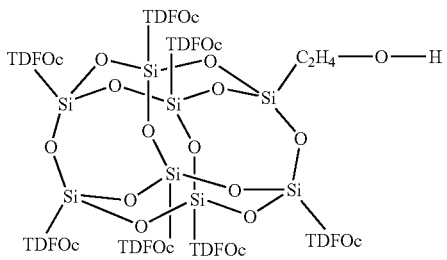

(157)

Example 74

Preparation of hydroxypropyl-heptatridecafluoro-1,1,2,2-tetrahydrooctyloctasilsesquioxane from a compound (156)

A compound represented by formula (158) can be prepared as in examples 54 to 58 except that the starting material is the compound (156) prepared in example 70 or 72.

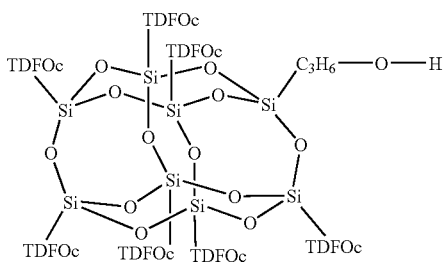

(158)

What is claimed is:

1. A production process for a silicon compound represented by formula (1), which comprises subjecting a silicon compound represented by formula (2) to hydrolysis or transesterification in the presence of an acid or basic catalyst,

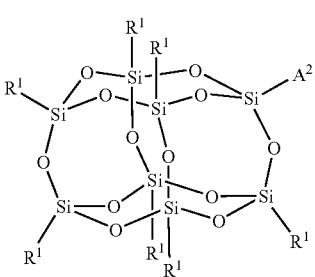

(1)

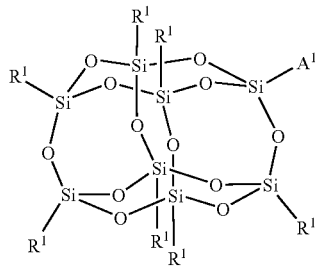

(2)

wherein in formula (1), each of seven $R^1$ is a functional group independently selected from the group consisting of (a) hydrogen, (b) alkyl wherein each hydrogen may be optionally substituted with fluorine and each —$CH_2$— group may be optionally replaced with —O—, —CH=CH—, cycloalkylene or cycloalkenylene, (c) substituted or unsubstituted aryl, and (d) substituted or unsubstituted arylalkyl wherein each hydrogen of the alkylene group may be optionally substituted with fluorine and each —$CH_2$— group of said alkylene may be optionally replaced with —O— or —CH=CH—; and $A^2$ is a hydroxyl-terminal orgainc functional group, and in formula (2), each $R^1$ is the same as $R^1$ in formula (1), and $A^1$ is an organic functional group containing an acyloxy group.

2. The production process according to claim 1, wherein each of seven $R^1$ in formula (1) is independently selected from the group consisting of: hydrogen; $C_1$–$C_{45}$ alkyl wherein each hydrogen may be optionally substituted with fluorine and each —$CH_2$— group may be optionally replaced with —O—, —CH=CH—, cycloalkylene, or cycloalkenylene; substituted or unsubstituted aryl; and substituted or unsubstituted arylalkyl wherein each hydrogen of the alkylene is optionally substituted with fluorine and each —$CH_2$— group of said alkylene may be optionally replaced with —O— or —CH=CH—.

3. The production process according to claim 1, wherein each of seven $R^1$ formula (1) is independently selected from the group consisting of: hydrogen; and $C_1$–$C_{30}$ alkyl wherein each hydrogen may be optionally substituted with fluorine, and each —$CH_2$— group may be optionally replaced with —O— or cycloalkylene.

4. The production process according to claim 1, wherein each of seven $R^1$ in formula (1) is independently selected from the group consisting of: $C_1$–$C_{20}$ alkenyl wherein each hydrogen may be optionally substituted with fluorine and each —$CH_2$— group may be optionally replaced with —O— or cycloalkylene; and $C_1$–$C_{20}$ alkyl wherein each —$CH_2$— group is optionally replaced with cycloalkenylene and in the —$CH_2$— group optionally replaced with cycloalkylene, each hydrogen may be optionally substituted with fluorine.

5. The production process according to claim 1, wherein each of seven $R^1$ in formula (1) is independently selected from the group consisting of: naphthyl; and phenyl wherein each hydrogen may be optionally substituted with halogen or $C_1$–$C_{10}$ alkyl where each hydrogen may be optionally substituted with fluorine and each —CH$_2$— group may be optionally replaced with —O—, —CH═CH—, cycloalkylene or phenylene.

6. The production process according to claim 1, wherein each of seven R$^1$ formula (1) is independently selected from the group consisting of phenylalkyls: wherein each hydrogen atom in a benzene ring may be optionally substituted with halogen or C$_1$–C$_{12}$ alkyl where each hydrogen may be optionally substituted with fluorine and each —CH$_2$— group may be optionally replaced with —O—, —CH═CH—, cycloalkylene or phenylene, and in the alkylene of the phenylalkyl, the number of carbons of the alkylene group is 1 to 12; each hydrogen of said alkylene group may be optionally substituted with fluorine; and each —CH$_2$— group of said alkylene group may be optionally replaced with —O— or —CH═CH—.

7. The production process according to claim 1, wherein each of seven R$^1$ in formula (1) is independently selected from the group consisting of C$_1$–C$_8$ alkyl wherein each hydrogen may be optionally substituted with fluorine and each —CH$_2$— group may be optionally replaced with —O—, —CH═CH—, cycloalkylene or cycloalkenylene; phenyl wherein each hydrogen may be optionally substituted with halogen, methyl or methoxy; unsubstituted naphthyl; and phenylalkyl wherein (a) each phenyl hydrogen may be optionally substituted with fluorine, C$_1$–C$_4$ alkyl, ethenyl or methoxy, (b) the number of carbons of the alkylene is 1 to 8, and each —CH$_2$— group of said alkylene may be optionally replaced with —O— or —CH═CH—.

8. The production process according to claim 1, wherein all of seven R$^1$ in formula (1) are the same functional groups selected from the group consisting of: C$_1$–C$_8$ alkyl wherein each hydrogen may be optionally substituted with fluorine and each —CH$_2$— group may be optionally replaced with —O—, —CH═CH—, cycloalkylene or cycloalkenylene; phenyl wherein each hydrogen may be optionally substituted with halogen, methyl or methoxy; unsubstituted naphthyl; and phenylalkyl wherein (a) each phenyl hydrogen may be optionally substituted with fluorine, C$_1$–C$_4$ alkyl, ethenyl or methoxy, (b) the number of carbons of the alkylene is 1 to 8, and each —CH$_2$— group of said alkylene may be optionally replaced with —O— or —CH═CH—.

9. The production process according to claim 1, wherein all of seven R$^1$ in formula (1) are the same functional groups selected from C$_1$–C$_8$ alkyls wherein each hydrogen may be optionally substituted with fluorine and each —CH$_2$— group may be optionally replaced with —O—, —CH═CH—, cycloalkylene, or cycloalkenylene.

10. The production process according to claim 1, wherein all of seven R$^1$ in formula (1) are the same functional groups selected from the group consisting of: phenyl wherein each hydrogen may be optionally substituted with halogen, methyl or methoxy; naphthyl; and phenylalkyl wherein (a) each hydrogen of the phenyl may be substituted with fluorine, C$_1$–C$_4$ alkyl, ethenyl or methoxy, (b) the number of carbons of the alkylene group is 1 to 8, and each —CH$_2$— group of said alkylene may be optionally replaced with —O—.

11. The production process according to claim 1, wherein A$^2$ in formula (1) is a group represented by formula (3), and A$^1$ in formula (2) is a group represented by formula (4),

wherein:

in formula (3), Z$^1$ is (a) C$_1$–C$_{22}$ alkylene where each —CH$_2$— may be optionally replaced with —O—, or (b) C$_3$–C$_8$ alkenylene where each —CH$_2$— may be optionally replaced with —O—; and in formula (4), R$^2$ is selected from the group of C$_1$–C$_{17}$ alkyl where each hydrogen may be optionally substituted with fluorine, C$_2$–C$_3$ alkenyl, substituted or unsubstituted phenyl and unsubstituted phenylalkyl.

12. The production process according to claim 1, wherein A$^2$ in formula (1) is a group represented by formula (5), and A$^1$ in formula (2) is a group represented by formula (6),

wherein:

in formula (5), (a) Z$^2$ represents a single bond or C$_1$–C$_3$ alkylene and may be bound to the benzene ring at any position, (b) Z$^3$ is (i) C$_1$–C$_{22}$ alkylene where each —CH$_2$— may be optionally replaced with —O— or (ii) C$_3$–C$_8$ alkenylene where each —CH$_2$— may be optionally replaced with —O—, and in formula (6), R$^2$ is selected from the group consisting of C$_1$–C$_{17}$ alkyl, C$_2$–C$_3$ alkenyl, substituted or unsubstituted phenyl and unsubstituted phenylalkyl, and Z$^2$ and Z$^3$ are the same as Z$^2$ and Z$^3$ in formula (5).

13. The production process according to claim 11, wherein: Z$^1$ in formula (3) is C$_1$–C$_{22}$ alkylene where each —CH$_2$— group may be optionally replaced with —O—; and R$^2$ in formula (4) is selected from the group consisting of C$_1$–C$_{17}$ alkyl where each hydrogen may be optionally substituted with fluorine, and C$_2$–C$_3$ alkenyl where each —CH$_2$— group may be optionally replaced with —O—.

14. The production process according to claim 11, wherein Z$^1$ in formula (3) is C$_1$–C$_6$ straight-chain alkylene where each —CH$_2$— group may be optionally replaced with —O—; and R$^2$ in formula (4) is methyl.

15. The production process according to claim 12, wherein $Z^2$ in formula (5) represents a single bond or $C_1$–$C_3$ alkylene where each —$CH_2$— group may be optionally replaced with —O—, and $Z^3$ is $C_1$–$C_{22}$ alkylene where each —$CH_2$— group may be optionally replaced with —O— and may be bound to the benzene ring at any carbon position; and $R^2$ in formula (6) is selected from the group consisting of (a) $C_1$–$C_{17}$ alkyl where each hydrogen may be optionally substituted with fluorine and each —$CH_2$— group may be optionally replaced with —O—, and (b) $C_2$–$C_3$ alkenyl where each —$CH_2$— group may be optionally replaced by —O—.

16. The production process according to claim 12, wherein $Z^2$ in formula (5) represents a single bond or —$CH_2$—, $Z^3$ in formula (5) is —$C_2H_4$—, and $R^2$ in formula (6) is methyl.

17. The production process according to claim 1, wherein all of seven $R^1$ in formula (1) are the same groups selected from the group consisting of ethyl, 2-methylpropyl, 2,4,4-trimethylpentyl, cyclopentyl, cyclohexyl, trifluoropropyl, tridecafluoro-1,1,2,2-tetrahydrooctyl, and unsubstituted phenyl.

18. The production process according to claim 1, wherein all of seven $R^1$ in formula (1) are either unsubstituted phenyl or trifluoropropyl.

19. The production process according to claim 1, characterized by providing a silicon compound represented by formula (2) through reacting a trichlorosilane compound having an acyloxy group with either (a) a compound represented by formula (7) or (b) a compound represented by formula (12) and acid-catalyzed transesterificating in alcohol,

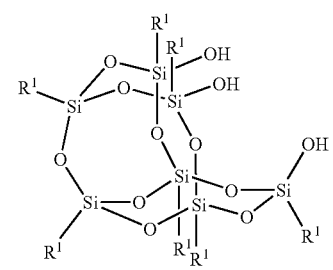
(7)

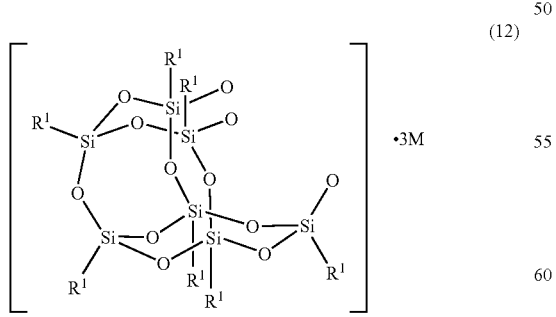
(12)

wherein: in formulas (7) and (12), $R^1$ is the same as $R^1$ in formula (1) and M is a monovalent alkali metal atom.

20. The production process according to claim 11, characterized by providing a silicon compound represented by formula (10) through reacting a compound represented by formula (8) with a compound represented by formula (7) and acid-catalyzed transesterificating in alcohol,

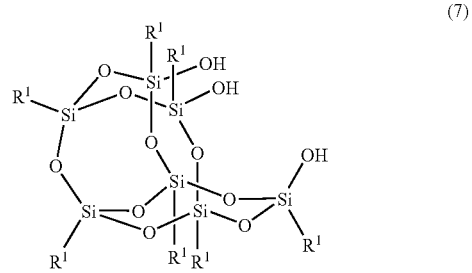
(7)

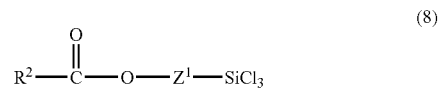
(8)

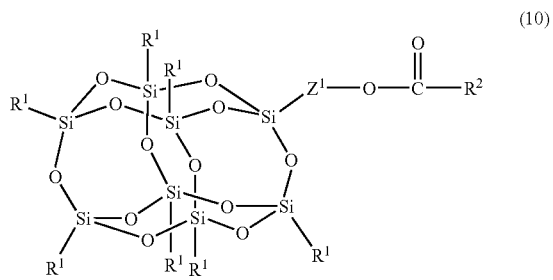
(10)

wherein: in formula (7), $R^1$ is the same as $R^1$ in formula (1) as described in claim 1, in formula (8), $R^2$ and $Z^1$ are the same as $R^2$ and $Z^1$ in formula (4) as described in claim 11, and in formula (10), $R^1$, $R^2$ and $Z^1$ are the same as $R^1$, $R^2$ and $Z^1$ in formulas (7) and (8).

21. The production process according to claim 12, characterized by providing a silicon compound represented by formula (11) through reacting a compound represented by formula (9) with a compound represented by formula (7) and acid-catalyzed transesterificating in alcohol,

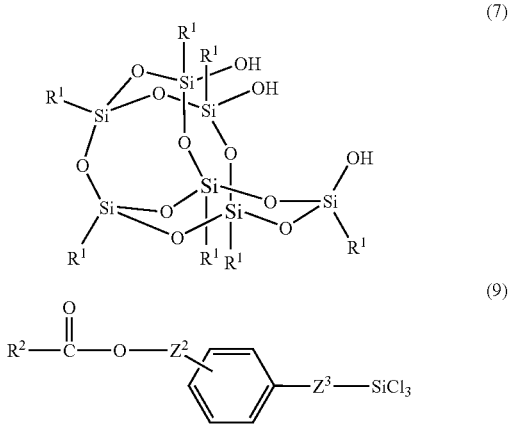
(7)

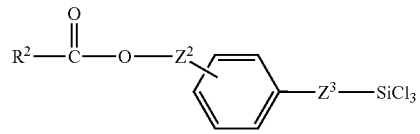
(9)

-continued (11)

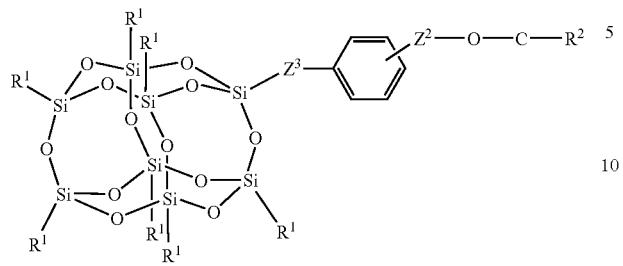

wherein: in formula (7), $R^1$ is the same as $R^1$ in formula (1) as described in claim 1, in formula (9), $R^2$, $Z^2$, and the binding position thereof to the benzene ring are the same as $R^2$, $Z^2$, and the binding position thereof to the benzene ring in formula (6) as described in claim 12, and in formula (11), the characters and the binding position thereof to the benzene ring are the same as the characters and the binding position thereof to the benzene ring in formulas (7) and (9).

22. The production process according to claim 11, characterized by providing a silicon compound represented by formula (10) through reacting a compound represented by formula (8) with a compound represented by formula (7) and acid-catalyzed transesterificating in alcohol, (7)

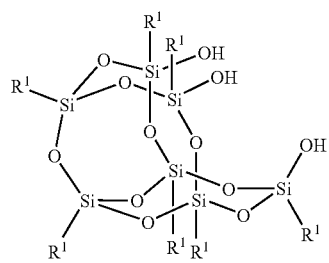

(8)

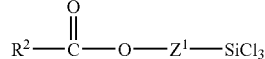

(10)

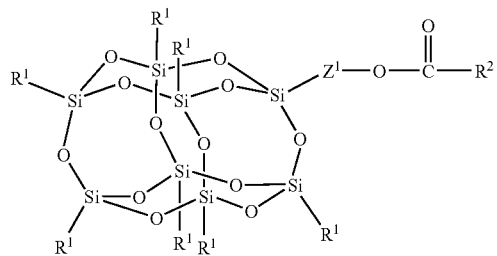

wherein: in formula (7), all of seven $R^1$ are the same functional groups selected from the group consisting of ethyl, 2-methylpropyl, 2,4,4-trimethylpentyl, cyclopentyl, cyclohexyl, trifluoropropyl, tridecafluoro-1,1,2,2-tetrahydrooctyl and unsubstituted phenyl, in formula (8), $R^2$ and $Z^1$ are the same as $R^2$ and $Z^1$ in formula (4) as described in claim 11, and in formula (10), $R^1$, $R^2$ and $Z^1$ are the same as $R^1$, $R^2$ and $Z^1$ in formula (7) and (8).

23. The production process according to claim 11, characterized by providing a silicon compound represented by formula (10) through reacting a compound represented by formula (8) with a compound represented by formula (12) and acid-catalyzed transesterificating in alcohol, (12)

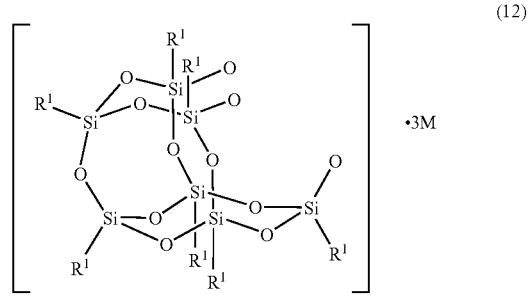

(8)

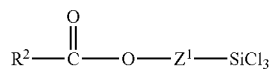

(10)

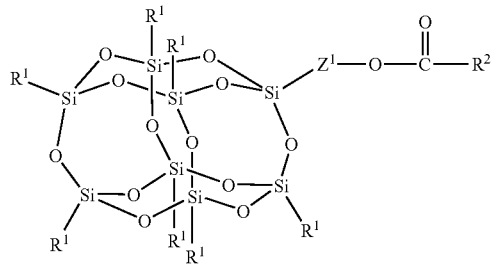

wherein: in formula (12), $R^1$ is the same as $R^1$ in formula (1) as described in claim 1 and M is a monovalent alkali metal atom, in formula (8), $R^2$ and $Z^1$ are the same as $R^2$ and $Z^1$ in formula (4) as described in claim 11, and in formula (10), $R^1$, $R^2$, and $Z^1$ are the same as $R^1$, $R^2$, and $Z^1$ in formulas (12) and (8).

24. The production process according to claim 12, characterized by providing a silicon compound represented by formula (11) through reacting a compound represented by formula (9) with a compound represented by formula (12) and acid-catalyzed transesterificating in alcohol, (12)

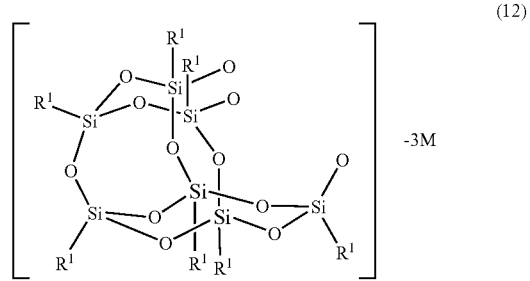

(9)

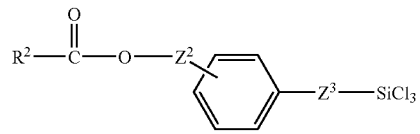

-continued (11)

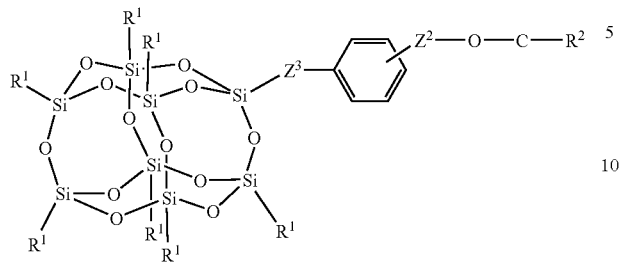

wherein: in formula (12), $R^1$ is the same as $R^1$ in formula (1) as described in claim 1 and M is a monovalent alkali metal atom, in formula (9), $R^2$, $Z^2$, $Z^3$, and the binding position thereof to the benzene ring are the same as $R^2$, $Z^2$, $Z^3$, and the binding position thereof to the benzene ring in formula (6) as described in claim 12, and in formula (11), the characters and the binding position thereof to the benzene ring are the same as the characters and the binding position thereof to the benzene ring in formulas (12) and (9).

25. The production process according to claim 11, characterized by providing a silicon compound represented by formula (10) through reacting a compound represented by formula (8) with a compound represented by formula (12) and acid-catalyzed transesterificating in alcohol, (12)

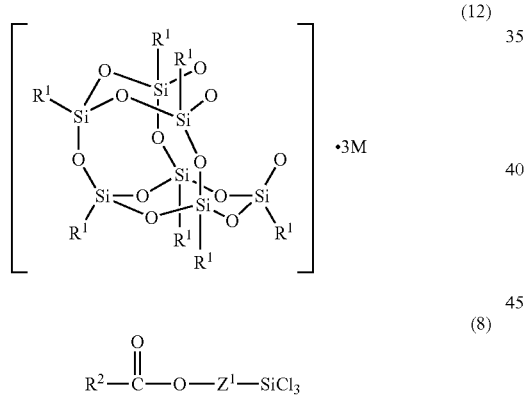

(8)

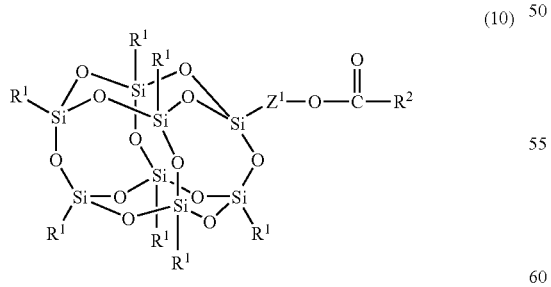

(10)

wherein: in formula (12), all of seven $R^1$ are the same groups selected from the group consisting of (i) $C_1$–$C_8$ alkyl where each hydrogen may be optionally substituted with fluorine and each —$CH_2$— group may be optionally replaced with —O—, —CH=CH—, cycloalkylene or cycloalkenylene, (ii) phenyl where each hydrogen may be optionally substituted with halogen, methyl or methoxy, (iii) unsubstituted naphthyl and (iv) phenylalkyl where (A) each benzene hydrogen may be substituted with fluorine, $C_1$–$C_4$ alkyl, ethenyl or methoxy, (B) each —$CH_2$— group of the alkylene may be optionally replaced with —O— or —CH=CH—, and M is a monovalent alkali metal atom, in formula (8), $R^2$ and $Z^1$ are the same as $R^2$ and $Z^1$ in formula (4) as described in claim 11, and in formulas (12) and (8).

26. The production process according to claim 11, characterized by providing a silicon compound represented by formula (10) through reacting a compound represented by formula (8) with a compound represented by formula (12) and acid-catalyzed transesterificating in alcohol, (12)

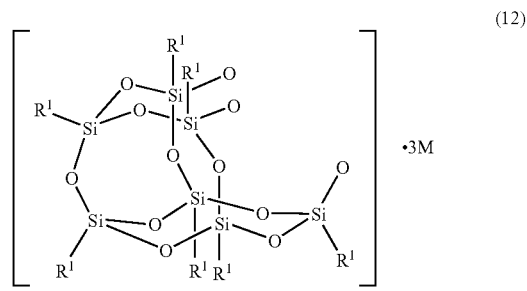

(8)

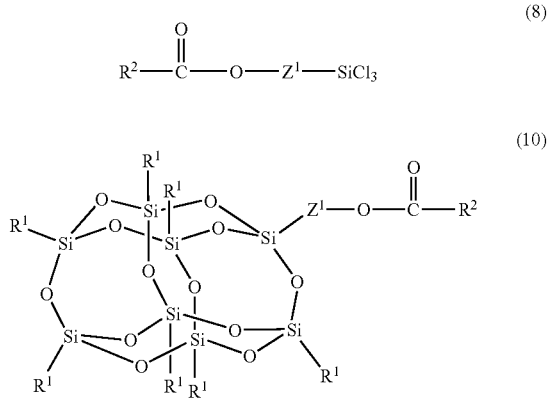

(10)

wherein: in formula (12), all of seven $R^1$ are the same groups selected from the group consisting of (i) ethyl, (ii) 2-methylpropyl, (iii) 2,4,4,-trimethylpentyl, (iv) cyclopentyl, (v) cyclohexyl, (vi) trifluoropropyl, (vii) tridecafluoro-1,1,2,2-tetrahydrooctyl, and (viii) unsubstituted phenyl, and M is a monovalent alkali metal atom, in formula (8), $R^7$ and $Z^1$ are the same as $R^2$ and $Z^1$ in formula (4) as described in claim 11 of formula (10), $R^1$, defined below through reaction of (a) a compound of formula (12), and in formula (10), $R^1$, $R^2$ and $Z^1$ are the same as $R^1$, $R^2$ and $Z^1$ in formulas (12) and (8).

27. The production process according to claim 12, characterized by providing a silicon compound represented by formula (11) through reacting a compound represented by formula (9) with a compound represented by formula (12) and acid-catalyzed transesterificating in alcohol,

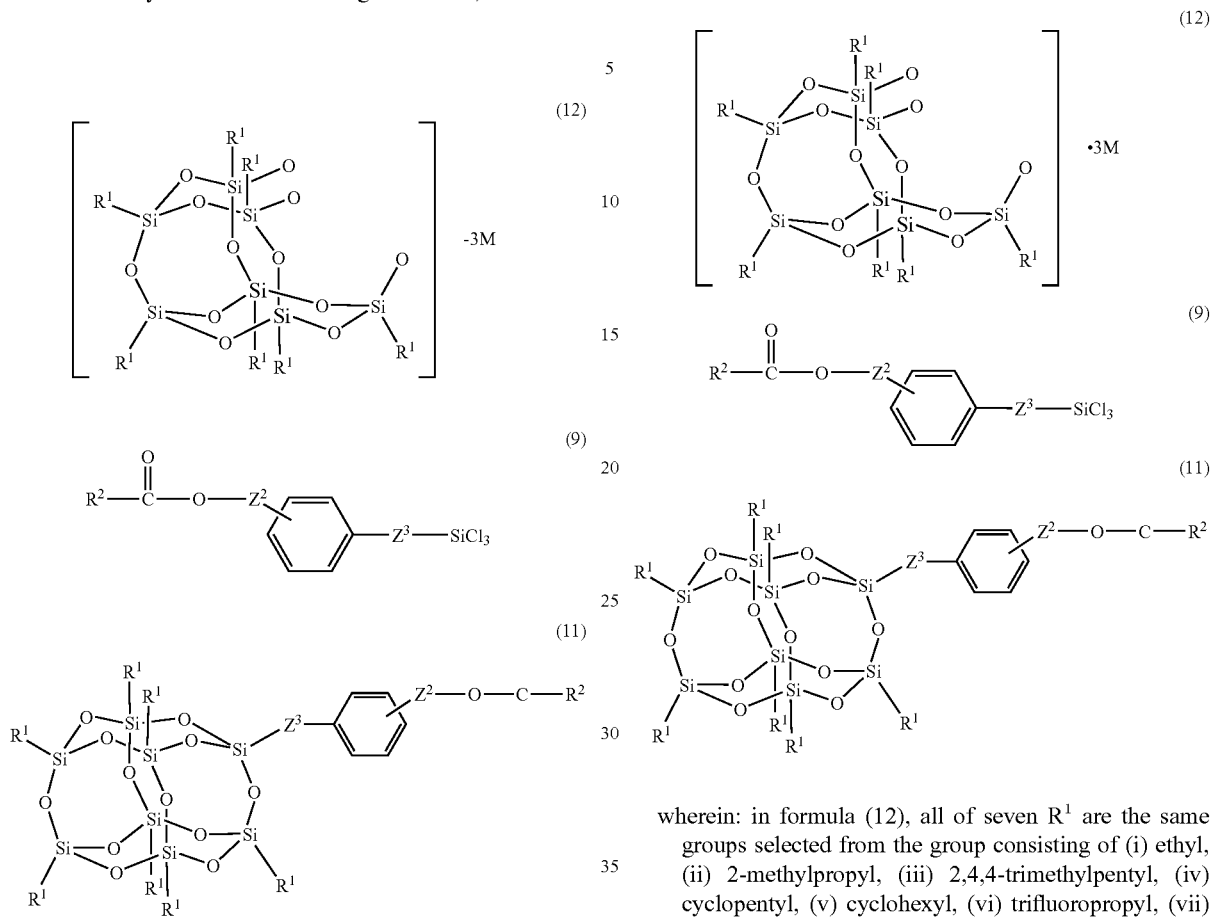

wherein: in formula (12), all of seven $R^1$ are the same groups selected from the group consisting of (i) $C_1$–$C_8$ alkyl wherein each hydrogen may be optionally substituted with fluorine and each —$CH_2$— group may be optionally replaced with —O—, —CH=CH—, cycloalkylene or cycloalkenylene, (ii) phenyl wherein each hydrogen may be optionally substituted with halogen, methyl or methoxy, (iii) unsubstituted naphthyl and (iv) phenylalkyl wherein each benzene hydrogen is optionally substituted with fluorine, $C_1$–$C_4$ alkyl, ethenyl or methoxy and each —$CH_2$— group of the akylene may be optionally replaced with —O— or —CH=CH—, and M is a monovalent alkali metal atom, in formula (9), $R^2$, $Z^2$, $Z^3$, and the binding position thereof to the benzene ring and are the same as $R^2$, $Z^2$, $Z^3$, and the binding position thereof to the benzene ring in formula (6) as described in claim 12, and in formula (11), the characters and the binding position thereof to the benzene ring are the same as the characters and the binding position thereof to the benzene ring in formulas (12) and (9).

28. The production process according to claim 12, characterized by providing a silicon compound represented by formula (11) through reacting a compound represented by formula (9) with a compound represented by formula (12) and acid-catalyzed transesterificating in alcohol, wherein: in formula (12), all of seven $R^1$ are the same groups selected from the group consisting of (i) ethyl, (ii) 2-methylpropyl, (iii) 2,4,4-trimethylpentyl, (iv) cyclopentyl, (v) cyclohexyl, (vi) trifluoropropyl, (vii) tridecafluoro-1,1,2,2-tetrahydrooctyl and (viii) unsubstituted phenyl, and M is a monovalent alkali metal atom, in formula (9), $R^2$, $Z^2$, $Z^3$, and the binding position thereof to the benzene ring are the same as $R^2$, $Z^2$, $Z^3$, and the binding position thereof to the benzene ring in formula (6) as described in claim 12, and in formula (11), the characters and the binding position thereof to the benzene ring are the same as the characters and the binding position thereof to the benzene ring in formulas (12) and (9).

29. The production process according to claim 12, characterized by providing a silicon compound represented by formula (11) through reacting a compound represented by formula (9) with a compound represented by formula (12) and acid-catalyzed transesterificating in alcohol,

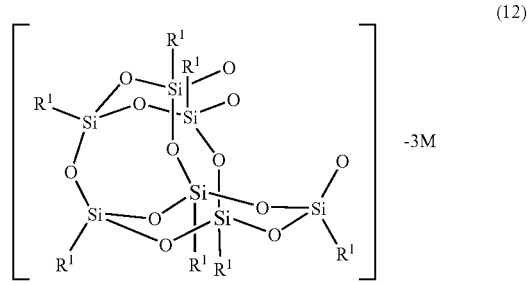

-continued

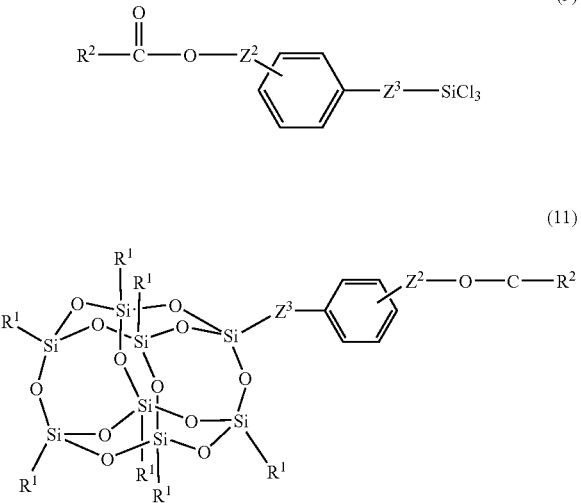

wherein: in formula (12), all of seven $R^1$ are either unsubstituted phenyl or trifluoropropyl and M is a monovalent alkali metal atom, in formula (9), $R^2$, $Z^2$, $Z^3$, and the binding position thereof to the benzene ring are the same as $R^2$, $Z^2$, $Z^3$, and the binding position thereof to the benzene ring in formula (6) as described in claim 12, and in formula (11), the characters and the binding position thereof to the benzene ring are the same as the characters and the binding position thereof to the benzene ring in formulas (12) and (9).

30. The production process according to claim 12, characterized by providing a silicon compound represented by formula (11) through reacting a compound represented by formula (9) with a compound represented by formula (7) and acid-catalyzed transesterificating in alcohol,

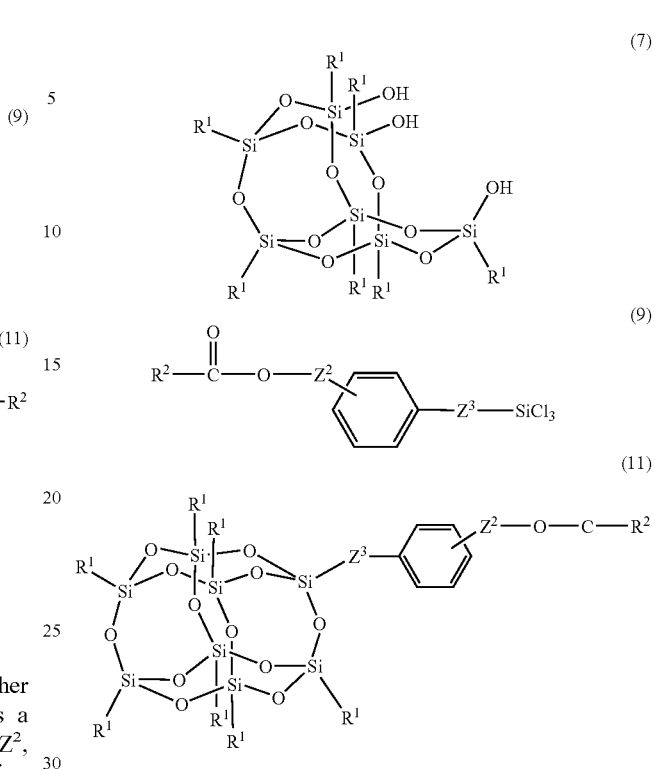

wherein: in formula (7), all of seven $R^1$ are the same group selected from the group consisting of (i) ethyl, (ii) 2-methylpropyl, (iii) 2,4,4-trimethylpentyl, (iv) cyclopentyl, (v) cyclohexyl, (vi) trifluoropropyl, (vii) tridecafluoro-1,1,2,2-tetrahydrooctyl and (viii) unsubstituted phenyl, in formula (9), $R^2$, $Z^2$, $Z^3$, and the binding position thereof to the benzene ring are the same as $R^2$, $Z^2$, $Z^3$, and the binding position thereof to the benzene ring in formula (6) as described in claim 12, and in formula (11), the characters and the binding position thereof to the benzene ring are the same as the characters and the binding position thereof to the benzene ring in formulas (7) and (9).

* * * * *